United States Patent
Penkler et al.

(10) Patent No.: US 6,551,619 B1
(45) Date of Patent: Apr. 22, 2003

(54) PHARMACEUTICAL CYCLOSPORIN FORMULATION WITH IMPROVED BIOPHARMACEUTICAL PROPERTIES, IMPROVED PHYSICAL QUALITY AND GREATER STABILITY, AND METHOD FOR PRODUCING SAID FORMULATION

(75) Inventors: Lawrence John Penkler, Port Elizabeth (ZA); Rainer Helmut Müller, Berlin (DE); Stephan Anton Runge, Eckernfoerde (DE); Vittorino Ravelli, Milan (IT)

(73) Assignee: Pharmatec International S.R.L., Milane (IT)

( * ) Notice: Subject to any disclaimer, the term of this patent is extended or adjusted under 35 U.S.C. 154(b) by 0 days.

(21) Appl. No.: 09/674,417

(22) PCT Filed: Apr. 29, 1999

(86) PCT No.: PCT/EP99/02892

§ 371 (c)(1),
(2), (4) Date: Jan. 22, 2001

(87) PCT Pub. No.: WO99/56733

PCT Pub. Date: Nov. 11, 1999

(30) Foreign Application Priority Data

Apr. 30, 1998 (DE) .......................... 198 19 273

(51) Int. Cl.[7] .................... A61K 9/14; A61K 9/00; A61K 9/16; A61F 13/00; A01N 25/00
(52) U.S. Cl. .................. 424/489; 424/422; 424/423; 424/400; 424/484; 424/493; 424/496; 424/497; 424/500; 514/951; 514/969; 514/975
(58) Field of Search ................. 424/489, 422, 424/423, 400, 484, 493, 496, 497, 500; 514/951, 969, 975

(56) References Cited

U.S. PATENT DOCUMENTS

| 5,430,021 A | * | 7/1995 | Rudnic et al. ............... 514/14 |
| 5,576,016 A | * | 11/1996 | Amselem et al. ........... 424/450 |
| 5,716,639 A | * | 2/1998 | Carlsson et al. ............ 424/450 |

FOREIGN PATENT DOCUMENTS

| WO | WO 9913864 | 3/1999 | ............ A61K/9/00 |

* cited by examiner

Primary Examiner—Thurman K. Page
Assistant Examiner—Blessing M. Fubara
(74) Attorney, Agent, or Firm—Abelman, Frayne & Schwab

(57) ABSTRACT

The invention relates to solid, particulate lipid-based excipients which are loaded with cyclosporine. Said excipients have improved biopharmaceutical properties for cyclosporines in vivo, are of a better quality (in terms of fineness, homogeneity of the particles, inclusion of the medicament) and are more physically stable in the particulate formulation (no aggregation or gel formation). The invention also relates to a therapeutic treatment with cyclosporine formulations which produce an average blood level concentration in the steady state range of 300 ng/ml to over 1000 ng/ml, preferably over 800 ng/ml, especially up to 900 ng/ml, preferably 400 ng/ml to 800 ng/ml in the absence of high initial blood level concentrations essentially over 1500 ng/ml, especially over 1200 ng/ml. This blood level concentration is preferably maintained for an extended period of at least 5 hours, preferably at least 7 hours.

30 Claims, 10 Drawing Sheets

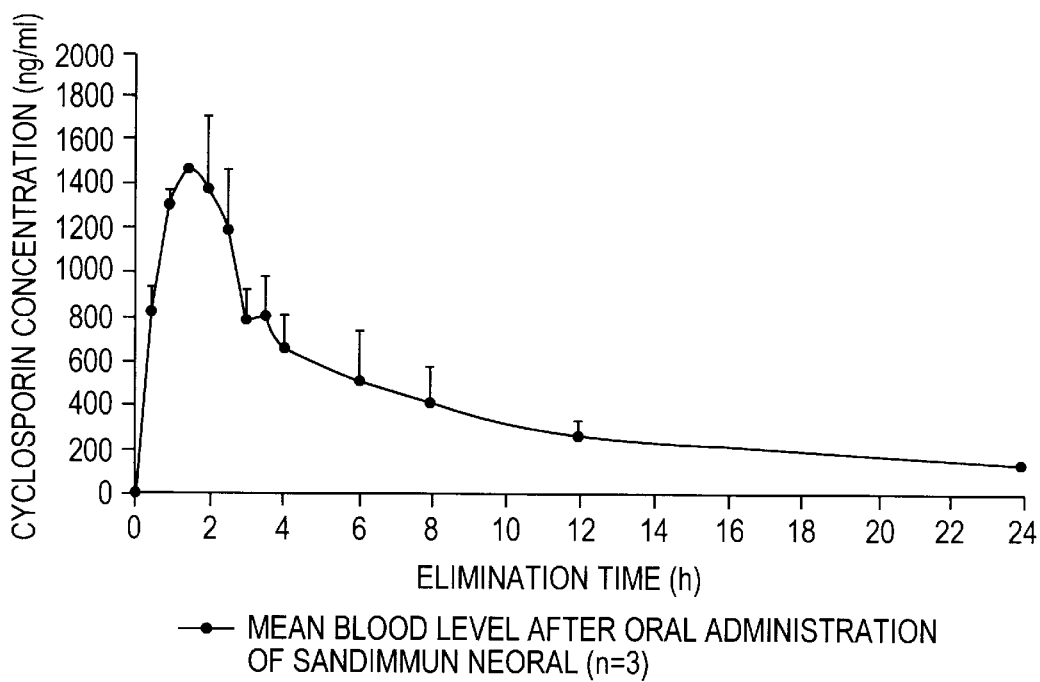
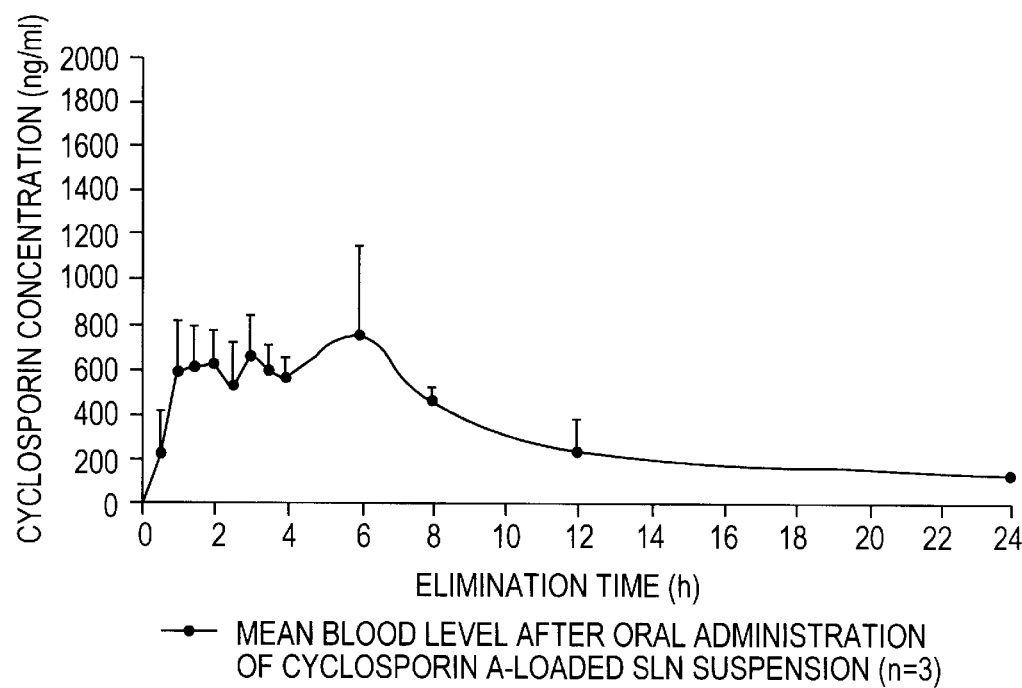
FIG. 2

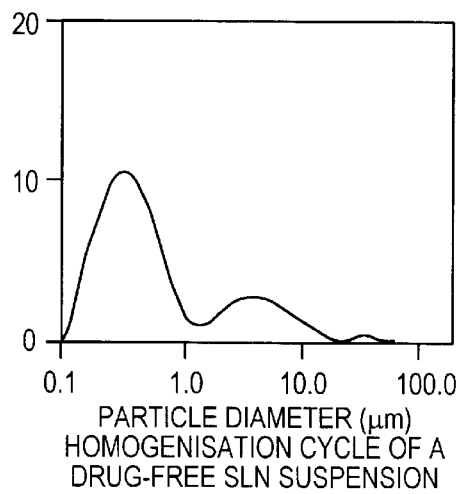
HOMOGENISATION CYCLE OF A
DRUG-FREE SLN SUSPENSION

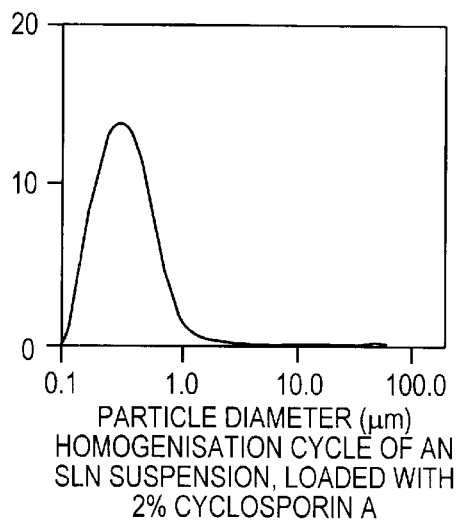
HOMOGENISATION CYCLE OF AN
SLN SUSPENSION, LOADED WITH
2% CYCLOSPORIN A

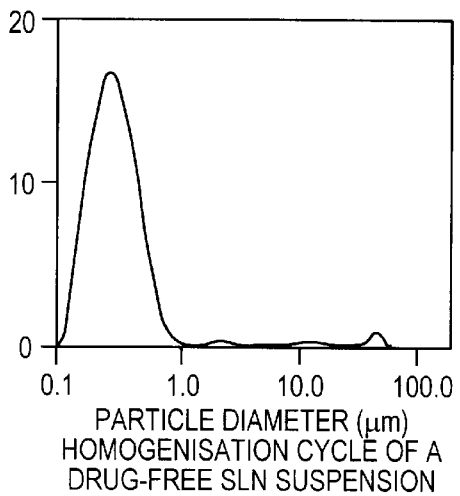
HOMOGENISATION CYCLE OF A
DRUG-FREE SLN SUSPENSION

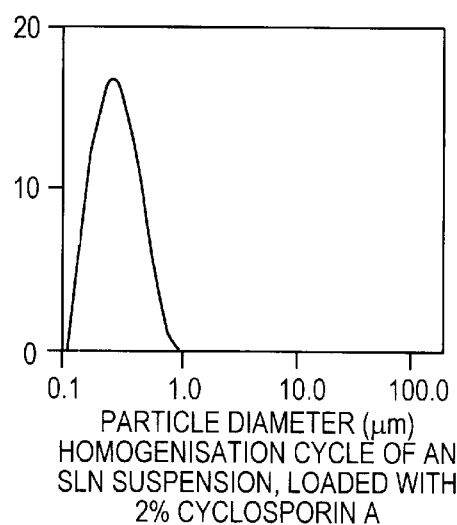
HOMOGENISATION CYCLE OF AN
SLN SUSPENSION, LOADED WITH
2% CYCLOSPORIN A

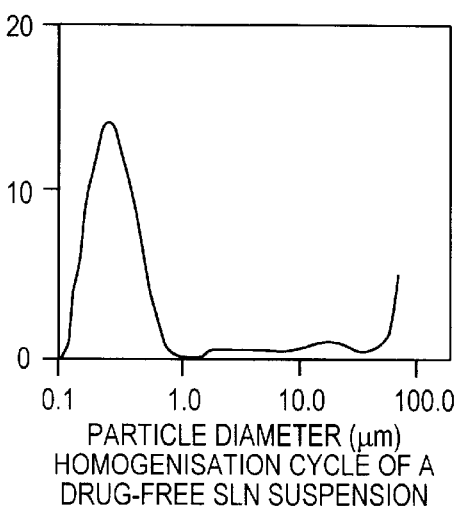
HOMOGENISATION CYCLE OF A
DRUG-FREE SLN SUSPENSION

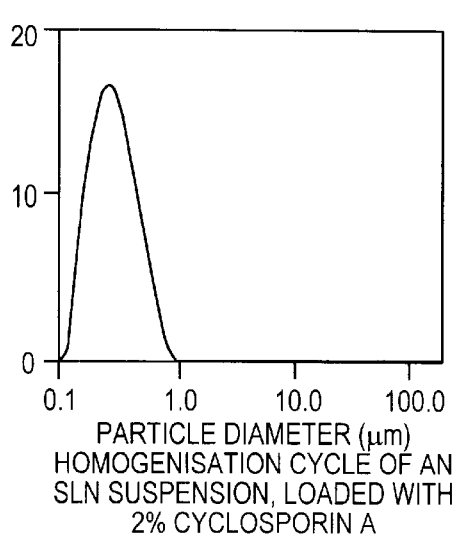
HOMOGENISATION CYCLE OF AN
SLN SUSPENSION, LOADED WITH
2% CYCLOSPORIN A

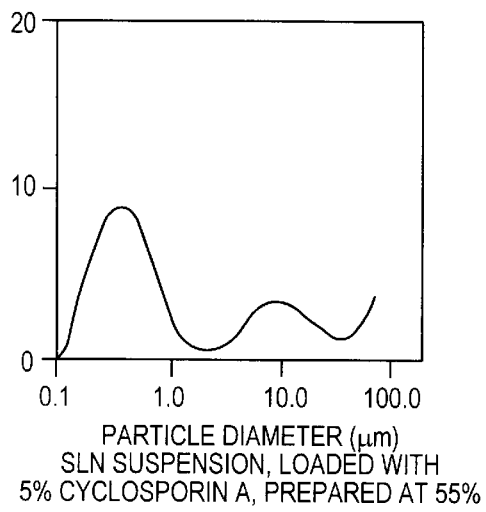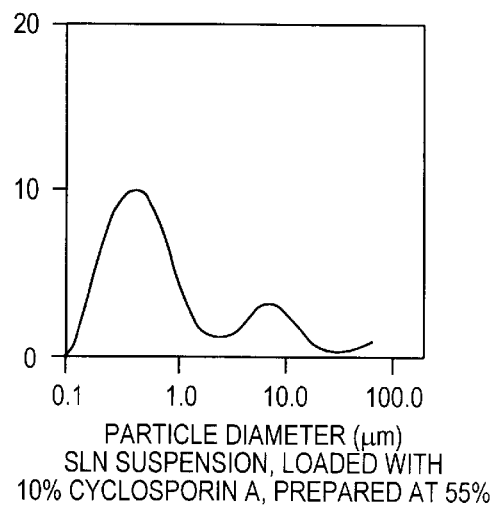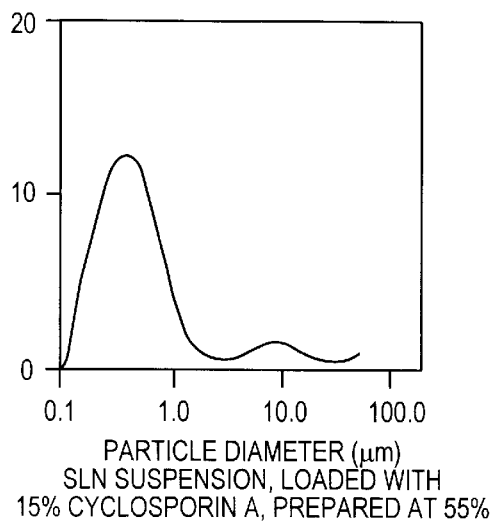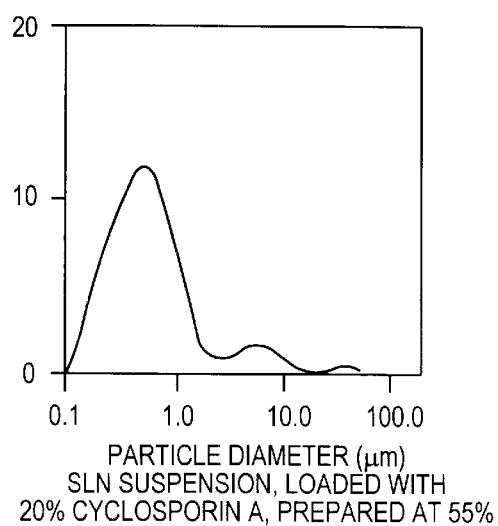
FIG. 4b

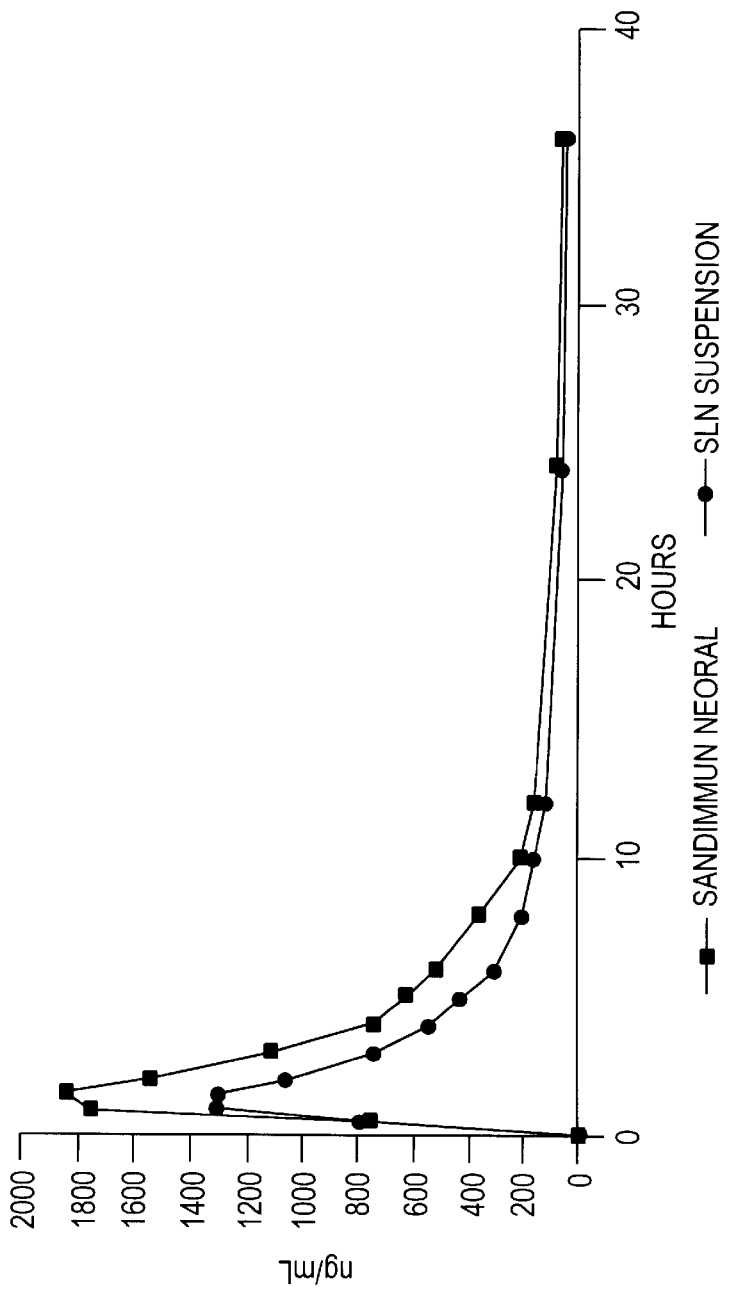
FIG. 9 BIOAVAILABILITY OF CYCLOSPORIN SLN BY COMPARISON WITH SANDIMMUN NEORAL AFTER A SINGLE ORAL ADMINISTRATION TO 9 HEALTHY VOLUNTEERS

PHARMACEUTICAL CYCLOSPORIN FORMULATION WITH IMPROVED BIOPHARMACEUTICAL PROPERTIES, IMPROVED PHYSICAL QUALITY AND GREATER STABILITY, AND METHOD FOR PRODUCING SAID FORMULATION

BACKGROUND OF THE INVENTION

1. Field of the Invention

The invention relates to particulate systems loaded with cyclosporin (also spelled "cyclosporine") or cyclosporin derivatives of natural and/or synthetic origin, which said systems have improved biopharmaceutical properties for cyclosporins in vivo, improved quality (fineness and homogeneity of the particles, drug inclusion) and improved physical stability of the particulate formulation (no aggregation or gel formation).

2. Description of the Related Art

Cyclosporins are cyclic oligopeptides. They are a group of natural oligopeptides ranging from cyclosporin A to cyclosporin Z. Synthetic derivatives have also been described (SDZ IMM 125, the hydroxyethyl derivative of D-serine-8-cyclosporin).

Cyclosporin A is a lipophilic molecule consisting of 11 aminoacids. It is obtained by fermenting mushrooms. Its molecular weight is 1203.

Commercial products: Sandimmun®, Sandimmun Optoral® (outside Germany=Sandimmun Neoral®) [A. Meinzer, E. Müller, J. Vonderscher, *Perorale Mikroemulsionsformulierung—Sandimmun Optoral®/Neorale®*, in: *Pharmazeutische Technologie: Moderne Arzneiformen*, R. H. Müller and G. E. Hildebrand (eds.), Wissenschaftliche Verlagsgesellschaft Stuttgart, 169–177, 1998]. Cyclosporin A is preferably used as an immunosuppressant after organ transplants. Other fields of use are autoimmune diseases, psoriasis and diabetes. All the cyclosporins (both natural and synthetic) can be used in the present invention.

The cyclosporins are highly lipophilic substances and poorly soluble in water (e.g. cyclosporin A: <0.004% m/V in water at 25° C.). Their high lipophilia and very poor solubility in water constitute the main problems in producing a suitable pharmaceutical preparation. In view of their better solubility in fatty oils and alcohol, Sandimmun® was developed with these ingredient as solubility enhancers for oral use in the form of an emulsion concentrate. The said emulsion concentrate consists of 100 mg cyclosporin dissolved in 1 ml of a mixture of oil, ethanol and an emulsifier, namely macrogol glycerol trioleate linolate. The concentrate must be diluted before use, for example by stirring it with a spoon into cold milk, cocoa or fruit juice. This non-standardised, inefficient mixing procedure results in the formation of a coarse non-homogenous oil/water emulsion with a relatively large droplet size. Its bioavailability after oral administration varies in vivo, in extreme cases between 10 and 60% [T. Beveridge, A. Gratwohl, F. Michot et al., *Curr. Ther. Res.*, 30 (5), 1981].

In addition to the oral solution formulation, Sandimmun® is also available in capsule form. The capsules contain 25 mg/100 mg cyclosporin A dissolved in a mixture of oil, ethanol and emulsifier. In this case, the oily preparation is dispersed in the stomach by peristaltic movements. Here again, this is an inefficient oil dispersion procedure.

Alternatively, the oily phase loaded with cyclosporin A has been treated in further experiments with high-pressure homogenisation. This process produced a finer O/W emulsion [Dietl, H., Pharmaceutical preparation containing cyclosporin(s) for oral administration and process for producing same, U.S. Pat. No. 5,637,317, 1997]. However, this patent contains no data relating to the physical stability of the homogenised emulsion during storage, nor in vivo data demonstrating that the homogenisation process can lead to increased bioavailability. It is known that when cyclosporin is dispersed in the oily phase of an O/W emulsion it precipitates after a few days, forming large crystals in the emulsion by crystallisation of the drug, or the cyclosporin that has exited from the oily phase floats, forming an edge or film on the surface. This problem is known, for example, in the case of the Sandimmun® oral emulsion. It is also known that the incorporation of a drug into the oily phase of an O/W emulsion can reduce the physical stability of the said emulsion in view of its tendency to coalesce [S. S. Davis, *Pharmaceutical aspects of i.v. fat emulsions*, J. Hosp. Pharm., 32, 149–170, 1974]. The small size of the droplets is not the only critical factor that causes increased bioavailability of cyclosporin. Homogenisation of the emulsion alone does not automatically increase bioavailability, as normal cyclosporin A re-absorption is also largely influenced by the secretion of bile salts [A. Meinzer, E. Müller, J. Vonderscher, *Perorale Mikroemulsionsformulierung— Sandimmun Optoral™/Neoral™*, in: *Pharmazeutische Technologie: Moderne Arzneiformen*, R. H. Müller and G. E. Hildebrand (eds.), Wissenschaftliche Verlagsgesellschaft Stuttgart, 1998]. Apart from the extent of bile salt release, food intake also constitutes a significant factor during drug absorption which can influence the bioavailability of cyclosporin. The release of drugs from emulsions also depends on the coefficient of distribution. This influence is difficult to control in order to obtain protracted, non-variable blood levels. These disadvantages of O/W emulsions (ie. coarse emulsions) have already been described for other cyclosporin emulsions [e.g. A. Tibell et al., *Cyclosporin A in fat emulsion carrier. Immunosuppressive effect in vitro*, J. Immunolo. 35, 231–236, 1992].

The next stage of development was the replacement of the Sandimmun® coarse emulsion formulation with the Sandimmun Optoral® microemulsion. The result was that absorption of cyclosporin A became nearly independent of bile salt secretion [A. Meinzer, E. Müller, J. Vonderscher, *Perorale Mikroemulsionsformulierung— Sandimmun Optoral™/Neoral™*, in: *Pharmazeutische Tecnologie: Moderne Arzneiformen*, R. H. Müller and G. E. Hildebrand (eds.), Wissenschaftliche Verlagsgesellschaft Stuttgart, 176, 1998]. A microemulsion does not contain separate droplets, but is a "critical solution" [B. W. Müller, *Mikroemulsionen als neue Wirkstofftragersysteme*, in *Pharmazeutische Technologie: Moderne Arzneiformen*, R. H. Müller and G. E. Hildebrand (eds.), Wissenschaftliche Verlagsgesellschaft Stuttgart, 161–168, 1998; B. W. Müller, H. J. Franzky, C. J. Kölln, U.S. Pat. No. 4,719,239, 1988]. Oral administration of the cyclosporin A microemulsion reduces the variability of absorption, although it produces high initial blood level peaks, well above the limit of 1000 ng/ml (FIG. 1, right). The said blood level peaks must be eliminated in an optimised preparation.

There are no effective topical preparations with cyclosporin A designed for topical treatment (e.g. psoriasis). In the literature, cyclosporin is said to have a topical action in theory (Clinical Report, Servizio de Medicina, Hospital del Cobre, Rancagua. Chile, *Rev. Med. Chil.* 1994, vol. 122; 1404–7]. However, its efficacy was only observed after six months' treatment; moreover, dimethyl sulphoxide had to be used as solvent at the concentration of 50%, which is unacceptable for a treatment like that of psoriasis. Theoretical therapeutic efficacy was also reported in another protocol (*Intralesional cyclosporine for psoriasis. Relationship of dose, tissue levels and efficacy.* J. Gajardo, J. Villaseca, *Arch. Dermatol.* 1992, vol. 128; 786–790). Topical application had no effect in this case, which demonstrates the importance of a suitable pharmaceutical form. Intralesional injections were therefore performed, and demonstrated the theoretical efficacy of the substance, although its use proved totally impracticable for treatment purposes.

SUMMARY

The main technical and biopharmaceutical problems of cyclosporin A formulations at present are:
1. the pharmaceutical quality and physical stability of the preparation (e.g. coarse emulsion, formation of cyclosporin A crystals and coalescence),
2. high variability of blood levels,
3. blood level peaks substantially >1500 or >1200 or >1000 ng/ml, which cause toxic side effects of various kinds,
4. ineffective topical formulations.

The objective of this invention is to eliminate the above said problems regarding the preparation and action of cyclosporin formulations. Alternatively, the invention can be used to prepare formulations that allow cyclosporin transport in the dermis in order to produce an effective topical treatment.

This objective is achieved by a drug carrier comprising solid lipid particles loaded with cyclosporin, and its use.

Absence of blood level peaks and extended release time are obtained with the use of fine particles of solid lipids. Unlike the liquid oily phase of an OW emulsion, because of the solid lipid matrix the release profile can be controlled by diffusion of the drug in the disintegrating lipid matrix.

In view of the lipophilic nature of the cyclosporin drug, lipids are preferred as the ideal candidates for incorporation into lipid particles as matrix material. Unlike polymer particles, lipid particles can be prepared on an industrial scale by high-pressure homogenisation [R. H. Müller and S. J. Lucks, Europ. Patent EP 0 605 497 B1, 1996].

The drug carrier is preferably prepared without halogenated organic solvents, and in particular without organic solvents at all.

The two basic preparation techniques are hot homogenisation and cold homogenisation [C. Schwarz, W. Mehnert, J. S. Lucks, R. H. Müller, *Solid lipid nanoparticles (SLN) for controlled drug delivery. I. Production, characterization and sterilization, J. Controlled. Rel.,* 30, 1994, 83–96].

In the hot homogenisation technique, the drug is first dissolved or finely dispersed in the molten lipid. The fat loaded with the drug is then dispersed in a hot solution of emulsifier at temperatures higher than the melting point of the lipid, and stirred to obtain a pre-emulsion. This coarse pre-emulsion is then dispersed by high-pressure homogenisation at pressures between 100 and 1500 bars in one or more homogenising cycles. High-pressure homogenisation also takes place at temperatures higher than the melting point of the lipid matrix. The nanoemulsion thus obtained is cooled, and the fat recrystallises to form solid lipid nanoparticles (SLN).

When the cold homogenisation technique is used, the fat remains in the solid state, ie. homogenisation takes place at temperatures lower than the melting point of the lipid. The fat containing the drug is reduced to microparticles in advance with a grinder such as a mortar grinder. The lipid particles thus obtained are then dispersed in a cold solution of emulsifier and homogenised by high-pressure homogenisation. The shearing forces and cavitation are strong enough to reduce the size of the solid lipid and form solid, ultrafine lipid particles called "solid lipid nanoparticles".

Both techniques have been used in the present invention to prepare lipid formulations loaded with cyclosporin.

BRIEF SUMMARY OF THE INVENTION

In particular, the drug carrier in accordance with the invention comprises particles, with or without surfactants, of a lipid or mixture of lipids having a particle size of between 10 nm and 100 µm which are solid at ambient temperature, in which the particles in the main population have a mean particle diameter of between 40 nm and 100 µm and can be obtained by dispersing an internal phase (lipid phase) in a dispersion medium (water, aqueous solution or a liquid miscible with water) in molten or softened form, or by dispersing an internal phase (lipid phase) in a dispersion medium in solid form and reducing the solid phase in size into fine particles before the dispersion process.

The particles in the solid state at ambient temperature preferably have a diameter of between 10 nm and 10 µm when prepared by high-pressure homogenisation; in this case the particles in the main population have a mean PCS particle diameter of between 40 nm and 1000 nm. The particles in the main population preferably have a mean particle diameter of between 100 nm and 500 nm, and the PCS particle diameters can be adjusted to between 40 nm and 100 nm by means of suitably selected process parameters and additives. The main population therefore constitutes the majority of the particles in the population.

Other size reduction procedures suitable for preparation of the drug carrier in accordance with the invention are high-speed stirring, exposure to ultrasound or a grinding process, especially with the use of jet-stream or airstream mills in which the solid particles in the main population have a mean particle diameter of between 0.5 µm and 100 µm (detected by laser diffractometry).

In order to keep the volume of the final preparation designed for oral administration sufficiently small, it is preferable to load the lipid matrix with 20% of cyclosporin A. Earlier experiments demonstrated that if the lipid matrix is strongly loaded with drug, for example with a 20% load of tetracaine, very coarse dispersions are obtained. Particle aggregation was promoted and a gelling process took place in the first few hours after preparation [A. zur Mühlen, C. Schwarz, W. Mehnert, *Solid lipid nanoparticles (SLN) for controlled drug delivery—drug release and release mechanism, Eur. J. Pharm. Biopharm.,* in press, 1998]. It was therefore expected that the manufacture of a dispersion of lipid particles with cyclosporin with relatively high drug loading of the lipid matrix of nanometric size, with high dispersity (=smal particle size) and sufficient physical stability, would have been very unlikely. However, the opposite effect was observed. The particle size of the cyclosporin-loaded lipid dispersion reduced as the cyclosporin content in the lipid matrix increased, and at the same time the polydispersity of the dispersion declined. Cyclosporin aids the formation of ultrafine lipid particles of small size with a high level of homogeneity. The addition of cyclosporin to the lipid matrix increases the pharmaceutical quality of the lipid nanoparticle dispersion; the optimum stability value is produced with a 20% (V/V) drug load.

The drug carrier in accordance with the invention therefore has an internal phase (lipid phase) content amounting to between 0.1% and 40% (m/m), and in particular between 1% and 20% (m/m), of the complete formulation.

Drug-loaded lipid nanoparticles have so far been generally described as physically unstable [C. Schwarz, *Feste Lipidnanopartikel: Herstellung, Charakterisierung Arzneistoffinkorporation und-freisetzung, Sterilisation und Lyophilisation,* Dissertationsschrift, Freie Universität Berlin, 1995]. The destabilisation of the said formulation takes place in three stages:

1. The lipid particles aggregate, as can easily be deduced from the increase in mean diameters.
2. The viscosity of the dispersion increases considerably, indicating progressive contact between the aggregates.
3. The lipid nanoparticles initially have a slightly creamy consistency; later, they form solid gels.

The gel consists of a lattice of lipid particles. It has been observed that gel formation is accompanied by a reduction in the fraction of variant α and a simultaneous increase in the fraction of variants β and β' [C. Freitas, R. H. Müller, *Long-term stability of solid lipid nanoparticles (SLN™). II. Influence of crystallinity of the lipid and shear forces,* submitted to *Eur. J. Pharm. Biopharm.* 1997].

Physically stable lipid particle dispersions (absence of aggregate and gel formation) presented little reduction, or even a slight increase, of the fraction of variant α during storage. In this case, no lipid portion was converted into variant β or β' [C. Freitas, R. H. Müller, *Long-term stability of solid lipid nanoparticles (SLN™). II. Influence of crystallinity of the lipid and shear forces,* submitted to *Eur. J. Pharm. Biopharm.* 1997]. It is known that the presence of pharmaceutical substances in the lipid matrix aids crystallisation in the most stable variant β or β' [B. Siekmann, *Untersuchungen zur Herstellung und zum Rekristallisationsverhalten schmelzemulgierter i.v. applizierbarer Glyceridnanopartikel,* Dissertationsschrift, Techn. Universität Carolo-Wilhelmins zu Braunschweig, 1994].

In the case of pure lipid particles, which normally remained in the liquid state after production and presented a slower recrystallisation process after days or weeks, recrystallisation could be accelerated by adding pharmaceutical substances. It was therefore expected that the incorporation of cyclosporin into the lipid matrix would destabilise the lipid particle dispersion. Surprisingly, however, the opposite occurred. The formation of variant β or β' was inhibited by cyclosporin A, and the fraction of variant α remained unchanged or actually increased slightly during storage. The particles loaded with cyclosporin A proved more physically stable than drug-free lipid particles, as can be seen from the smaller particle size and lower growth of the particles during storage. Cyclosporin acts as a stabiliser of lipid particles, and produces greater physical stability of the lipid dispersion.

The use of a lipid as drug carrier matrix presents considerable advantages in toxicological terms too. Most active principles of lipid nanoparticles have GRAS status or are accepted as GRAS substances (GRAS=generally regarded as safe) [*Food Additives— GRAS substances,* Food Drug Cosmetic Law Reports, Chicago, 1994]. All lipids in general, and all emulsifiers authorised for oral administration (e.g. tablets, capsules, pellets, oral solutions and suspensions) can be used for their preparation. Typical materials for the lipid matrix are glycerides of fatty acids present in foodstuffs and in the human body. The emulsifiers may be, for example, lecithin, sodium cholate, polysorbates such as polysorbate 80, or block copolymers such as Poloxamer 188 (an A-B-A block copolymer of polyethylene/polypropylene oxide with a relative mean molecular weight of 8350 g/mole, in which the mean relative molecular weight of the polyoxypropylene portion is 1750 g/mole and the polyoxyethylene portion is 80%). The said emulsifiers are even authorised for intravenous administration.

To sum up, in this invention a drug carrier or drug has been developed for an optimum treatment protocol with optimised blood levels, achieved with the use of ultrafine lipid particles loaded with cyclosporin A. Cyclosporin increases the physical quality of the particle dispersion by forming particularly fine particles with a high level of homogeneity. Physical stability also increases after the incorporation of cyclosporin into the lipid particles during storage of the particle dispersion.

BRIEF DESCRIPTION OF FIGURES

FIG. 2: Blood level of cyclosporin A after oral administration to pigs (mean value n=3, dose 16 mg/kg). Above: Sandimmun Neoral® as reference. Below: solid lipid particles loaded with cyclosporin (mean PCS particle diameter: 157 nm).

FIG. 3: Particle size distribution of drug-free SLN (left) and SLN loaded with cyclosporin A (right) obtained after 1, 3 and 5 homogenisation cycles at 85° C. (SLN preparation: 10% Imwitor 900 (a mixture of mono-, di- and triglycerides of palmitic and stearic acid, the monoglyceride portion being approx. 40%), 2.5% Tagat® S (polyoxyethylene glycerol monostearate), 0.5% sodium cholate and 87% water; in the case of a drug-loaded SLN suspension: 8% Imwitor 900 and 2% cyclosporin A, 2.5% Tagat® S, 0.5% sodium cholate and 87% water (y axis: frequency; x axis: $\mu$m; data obtained by laser diffractometry—LD).

FIG. 4a: Particle size distribution of SLN dispersions with an increased content of cyclosporin A, prepared by the hot homogenisation technique at 85° C. (cyclosporin load constituting 5%, 10%, 15% and 20% of the lipid matrix, formulations in Table 2, data obtained by laser diffractometry).

FIG. 4b: Particle size distribution of SLN dispersions with an increased content of cyclosporin A, prepared by the cold homogenisation technique at 55° C. (cyclosporin load constituting 5%, 10%, 15% and 20% of the lipid matrix, formulations in Table 2, data obtained by laser diffractometry).

FIG. 9: Bioavailability of SLN with cyclosporin compared to Sandimmun Neoral after a single oral administration to 9 healthy volunteers. The formulation of SLN with cyclosporin was prepared in accordance with example 1. The material (3 kg) was prepared in a Lab 60 APV homogeniser at a pressure of 200 bars with a continuous process at 85° C. for 20 mins. The formulation was administered to 9 healthy volunteers in suspension form with a cyclosporin A content equivalent to Sandimmun Neoral (300 mg). The mean blood levels are illustrated (top: Sandimmun Neoral; bottom: cyclosporin SLN suspension).

Examples of final formulation for patients: the liquid dispersion of the lipid particles can be spray-dried or freeze-dried. For oral administration, the dry power can be incorporated into sachets designed to be reconstituted to produce an oral suspension. The powder can also be incorporated into capsules or used to make tablets. Alternatively, the aqueous dispersion of SLN can be used after concentration of the aqueous phase for extrusion and pellet manufacture or in granulation for tablets. Parenteral administration, such as intravenous administration, is also possible. The ultrafine nature of the solid lipid nanoparticles prevents capillary blockade and therefore the risk of embolism.

Thanks to a drug carrier of this kind, the present invention solves the existing problems by means of provision of controlled, optimised blood values obtained with the use of a fine dispersion of physically stable solid lipid nanoparticles.

A special treatment has been developed to minimise the toxic side effects of cyclosporin and increase its therapeutic efficacy. Increased therapeutic efficacy has been achieved by reducing the variability of absorption and slowing release, with blood levels which remain stable for longer (steady state) in an optimised range of treatment. The mean optimized blood level produced by this invention prevents blood level peaks substantially >1500 ng/ml, in particular substantially >1200 ng/ml, preferably >1200 ng/ml, desirably >1000 ng/ml and ideally >800 ng/ml. The blood levels remain between 300 ng/ml and 900 ng/ml, and preferably between 400 ng/ml and 800 ng/ml, for a given period. The period for which the said blood levels of cyclosporin A remain unchanged is at least 5 hours, preferably 7 hours, and ideally over 8 hrs, with a blood concentration of the drug between 300 ng/ml and 900 ng/ml. The invention allows the preparation of topical formulations of cyclosporin A which promote the transport of cyclosporin A in the dermis.

Figure 1:
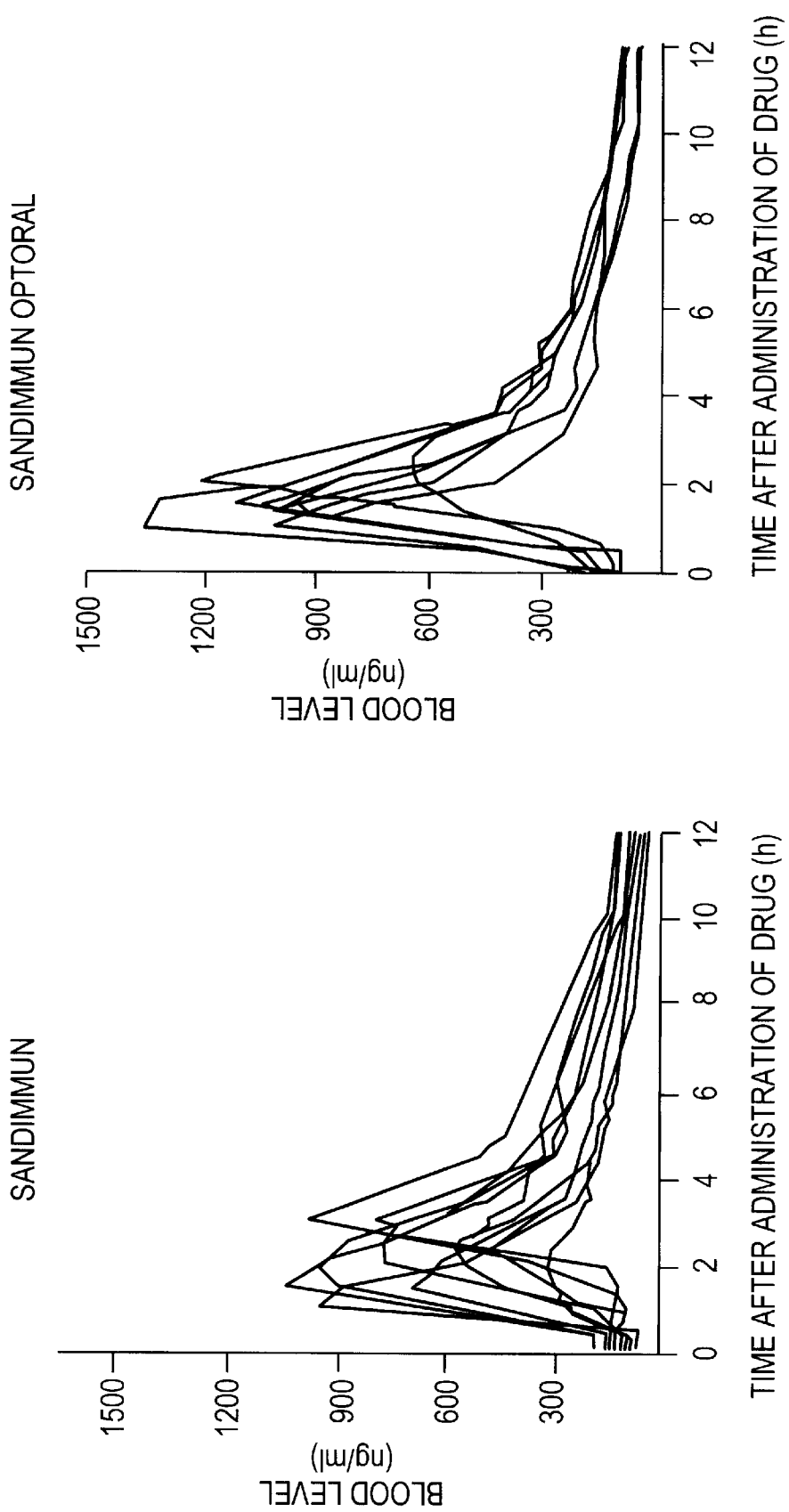
FIG. 1: Blood level of cyclosporin A after oral administration of Sandimmun® (left) and Sandimmun Neoral® (right) to patients who had undergone kidney transplants.

FIG. 1 (left) shows the variability of blood levels after oral administration of Sandimmun® to kidney transplant patients [according to A. Meinzer, E. Müller, J. Vonderscher, *Perorale Mikroemulsionsformulierung—Sandimmun Optoral™/Neoral™*, in *Pharmazeutische Technologie: Moderne Arzneiformen*, R. H. Müller and G. E. Hildebrand (eds.), Wissenschaftliche Verlagsgesellschaft Stuttgart, p. 175, 1998].

By way of comparison, FIG. 2 (bottom) shows the effect of the drug carrier in accordance with the invention or the type of treatment in accordance with the invention on the mean blood levels in a study conducted on three pigs (Example 1).

The mean blood levels produced by the said treatment in accordance with the invention present no peaks higher than 800 ng/ml for a time period of approx. 9 hrs, with blood levels of between 300 ng/ml and 900 ng/ml.

Biopharmaceutical characteristics: Oral administration of the cyclosporin-loaded drug carrier in accordance with this invention produces prolonged blood levels with low variability, absence of high, toxic peaks in the blood levels and therefore the absence or minimisation of side effects (such as cyclosporin-induced nephrotoxicity).

Quality of lipid particles: The solid lipid particles were prepared by dispersion of a cyclosporin-loaded lipid matrix in an emulsifier solution. The incorporation of cyclosporin into the lipid matrix improves the dispersity of the lipid and increases the fineness and homogeneity in size of the lipid particles after dispersion, compared to drug-free lipid particles prepared under the same conditions. The inclusion of the drug in the lipid particles can be increased by increasing the cyclosporin content of the formulation.

Physical stability: It has been demonstrated that aggregation of particles with gel formation (=destabilisation) in lipid dispersions is accompanied by transformation of the lipid from variant $\alpha$ to variant $\beta$ or $\beta'$. The incorporation of cyclosporin stabilises the formation of variant $\alpha$, thus preventing transformation into variant $\beta$ or $\beta'$ during storage and indicating greater physical stability of the particle dispersion.

The invention has been compared to the presently commercially available product Sandimmun Neoral®. FIG. 2 (top) shows the blood concentration curve after oral administration of the same dose. The mean blood level of Sandimmun Neoral® presents an initial blood level peak of approx. 1500 ng/ml and a blood level of between 300 and 900 ng/l for the period of 6 hrs only. In the direct comparison, both formulations—the microemulsion and the formulation in accordance with the invention (FIG. 2)—present minimal standard deviations and similar variability of bioavailability. However, the formulation in accordance with the invention prevents the high variability of blood levels caused by the Sandimmun® known to date (FIG. 1, left) and the high peaks of those values caused by Sandimmun Optoral® (FIG. 1, right and FIG. 2, top), and produces blood levels (steady state) which are more extended in time and with limited variability.

DETAILED DESCRIPTION OF THE INVENTION AND THE SUBSTANCES USED

The invention allows for an optimum treatment regimen; the optimum blood level thereof is obtained with the new drug carrier based on solid lipid particles loaded with cyclosporin. The lipid particles have been developed for oral and/or parenteral administration. The lipid matrix can contain one cyclosporin or a mixture of two or more cyclosporins of natural or synthetic origin. The lipid particles are preferably prepared by high-pressure homogenisation. A piston-gap homogeniser such as the one described in R. H. Müller and S. J. Lucks, European Patent EP 0 605 497 B1, 1996, can be used to obtain fine particles, preferably of nanometric size. Alternatively, homogenisation can be performed with a microfluidizer. To obtain lipid particles of a size between nanometres and a few micrometres (100 nm to 10 µm), dispersing of the lipid particles can be also effected at a lower power density, for example by treatment with ultrasound or high-speed stirrers. Alternatively, the dispersing can be effected with an airstream mill or by liquid grinding with a colloid mill.

Oily dispersions such as Sandimmun® present bioavailability varying between 10% and 60% [T. Beveridge, A. Gratwohl, F. Michot, W. Niederberger, E. Nüesch, K. Nussbaumer, P. Schaub and B. Speck, *Cyclosporin A: pharmacokinetics after a single dose in man and serum levels after multiple dosing in recipients of allogenic bone-marrow grafts*, Curr. Ther. Res. 30, 1981, 5–18]. The administration of a microemulsion in the form of a critical solution of cyclosporin (Sandimmun Optoral®) reduced the variation in bioavailability, but produced even higher blood level peaks after oral administration than Sandimmun® (FIG. 1, right). These high blood level peaks are responsible for the toxic side effects of cyclosporin A which may occur during treatment of patients, such as nephrotoxicity [Martindale, 29th edition, J. E. F. Reynolds (ed.), London, The Pharmaceutical Press, 1989].

Cyclosporin-loaded lipid particles are dispersions containing lipids, not solutions. As a result, it was expected that solid lipid particles loaded with cyclosporin would present the same, well-known variable bioavailability as the known preparation Sandimmun® containing lipids, and that the reproducibility of absorption would not increase. Surprisingly, the suspension of lipid particles loaded with cyclosporin (SLN) presented reproducibility of bioavailability similar to that of the preparation Sandimmun Neoral®, though without toxic peaks in the blood levels (FIG. 2). The SLN formulation also presented a prolonged release of the drug, and therefore longer lasting blood levels, between 400 ng/ml and 800 ng/l. These constant blood levels, without blood level peaks, constitute the optimum treatment regimen made possible by the invention. Blood cyclosporin levels of >1000 ng/ml, in particular >1200 ng/ml, in particular substantially >1500 ng/ml are considered critical in view of the toxic side effects. In clinical practice, the blood level should ideally be within the therapeutic range between 400 and 800 ng/ml.

The parameters used to evaluate the quality and toxicological acceptability of cyclosporin formulations are therefore the AUC (Area Under the Curve) percentages of the blood level which exceed 800 ng/l ($AUC_{>800}$ ng/ml) or 1000 ng/ml ($AUC_{>1000}$ ng/ml). As a result, the maximum concentration $C_{max}$ also constitutes an important parameter which should not exceed the concentration of 1000 ng/ml. A high initial blood level peak is undesirable; in other words, the time taken to reach $C_{max}$ (and also $T_{max}$) should not be too short, but should rather be detected at a later stage. In view of the retarded, uniform release of lipid particles loaded with cyclosporin, achivement of $T_{max}$ of lipid particles, in contrast to the reference Sandimmun Neoral® becomes detectable only later in time.

As shown in Table 1, the SLN formulation with cyclosporin in accordance with the invention satisfies the said requirements and gives evidence of the therapeutic improvement provided by the invention.

TABLE 1

Pharmacokinetic parameters of the SLN suspension with cyclosporin compared to Sandimmun Neoral ®: Percentage of $AUC_{>800\ ng/ml}$ and percentage of $AUC_{>1,000\ ng/ml}$, $C_{max}$ and $T_{max}$ (calculated on the basis of the mean blood level shown in FIG. 2). MV = mean value.

| | % $AUC_{>800\ ng/ml}$ | | % $AUC_{>1,000\ ng/ml}$ | | $C_{max}$ [ng/ml] | | $T_{max}$ [h] | |
|---|---|---|---|---|---|---|---|---|
| | SLN | Neoral ™ | SLN | Neoral ™ | SLN | Neoral ™ | SLN | Neoral ™ |
| MV (n = 3) | 0.4% | 6.5% | 1.7% | 11.7% | 745.7 | 1,467.7 | 6 | 1.5 |

The quality of the lipid particles (fineness and uniformity of size) is usually highest when the drug load is lowest [A. zur Mühlen, C. Schwarz, W. Mehnert, *Solid lipid nanoparticles (SLN) for controlled drug delivery—drug release and release mechanism*, Eur. J. Pharm. Biopharm., accepted, 1997]. In the case of model drugs such as tetracaine and hetomidate, an increased drug concentration has caused particle aggregation followed, in the case of a 10% hetomidate concentration, by gel formation [C. Schwarz, *Feste Lipidnanopartikel: Herstellung, Charakterisierung Arzneistoffinkorporation und-freisetzung, Sterilisation und Lyophilisation*, Dissertationsschrift, Freie Universität Berlin, 1995]. The opposite took place with a cyclosporin concentration increasing from 0% to 20% (Table 2, example 2):

1. The particle quality, measured on the basis of the size and distribution of drug-loaded SLNs, proved better than those of drug-free SLNs (ie. smaller, finer particles with narrow distribution).
2. An increasing drug load increased the quality of particles of the suspension (Table 3, example 2).

The production of a drug-free SLN suspension caused a broad distribution of particle sizes (measured by laser diffractometry) Over 25% of the particles were larger than 1 µm, with sizes of up to 80 µm (FIG. 3, top left). Three homogenisation cycles reduced the fraction of particles >1 µm, but without reducing the breadth of the distribution (FIG. 3, centre left). Five homogenisation cycles actually caused particle aggregation, recognisable by the increase in the values of the particle size distribution curve from 60 µm to 80 µm (FIG. 3, bottom left).

Conversely, with an SLN preparation loaded with cyclosporin, a single homogenisation cycle produced a very narrow particle size distribution, with a small percentage of particles >1 μm (approx. 5%) after loading of the lipid particles with 20% cyclosporin (FIG. 3, top right). Three homogenisation cycles produced an extremely homogenous distribution, with less than 1% of particles >1 μm (FIG. 3, centre right, Table 3 in example 2). The destabilisation observed in the drug-free SLN suspension (aggregation and formation of large particles) after five homogenisation cycles did not take place in the case of the cyclosporin-loaded particles. The size distribution was practically the same as the one after three homogenisation cycles (FIG. 3, centre right and bottom).

The lipid particles were prepared with increasing cyclosporin concentrations in relation to the lipid matrix, namely 5%, 10%, 15% and 20% (preparation: example 2, Table 2). The size analysis values of lipid particles prepared with the hot homogenisation technique are set out in Table 3 (example 2, data obtained with laser diffractometry, volume distribution values). The LD diameter d50% declined as the drug load increased; with a cyclosporin load amounting to 20% of the lipid matrix, the particle diameter d50% was 310 nm. A drastic reduction was detected for volume-based particle diameters amounting to d95% and d99%. Diameter d99% constitutes a highly sensitive parameter to demonstrate the dimensional uniformity of the particles. This parameter is particularly sensitive if the particle size is calculated on the basis of volume distribution. The considerable reduction demonstrates the reduction in the fraction of particles in the μm range, and therefore an increase in dimensional uniformity. Thus, for example, diameter d99% fell from approx. 60 μm (mean value of n=3, cyclosporin load 5% of lipid phase) to a value of 860 nm (mean value of n=3, cyclosporin load 20% of lipid matrix).

Figure 4A:
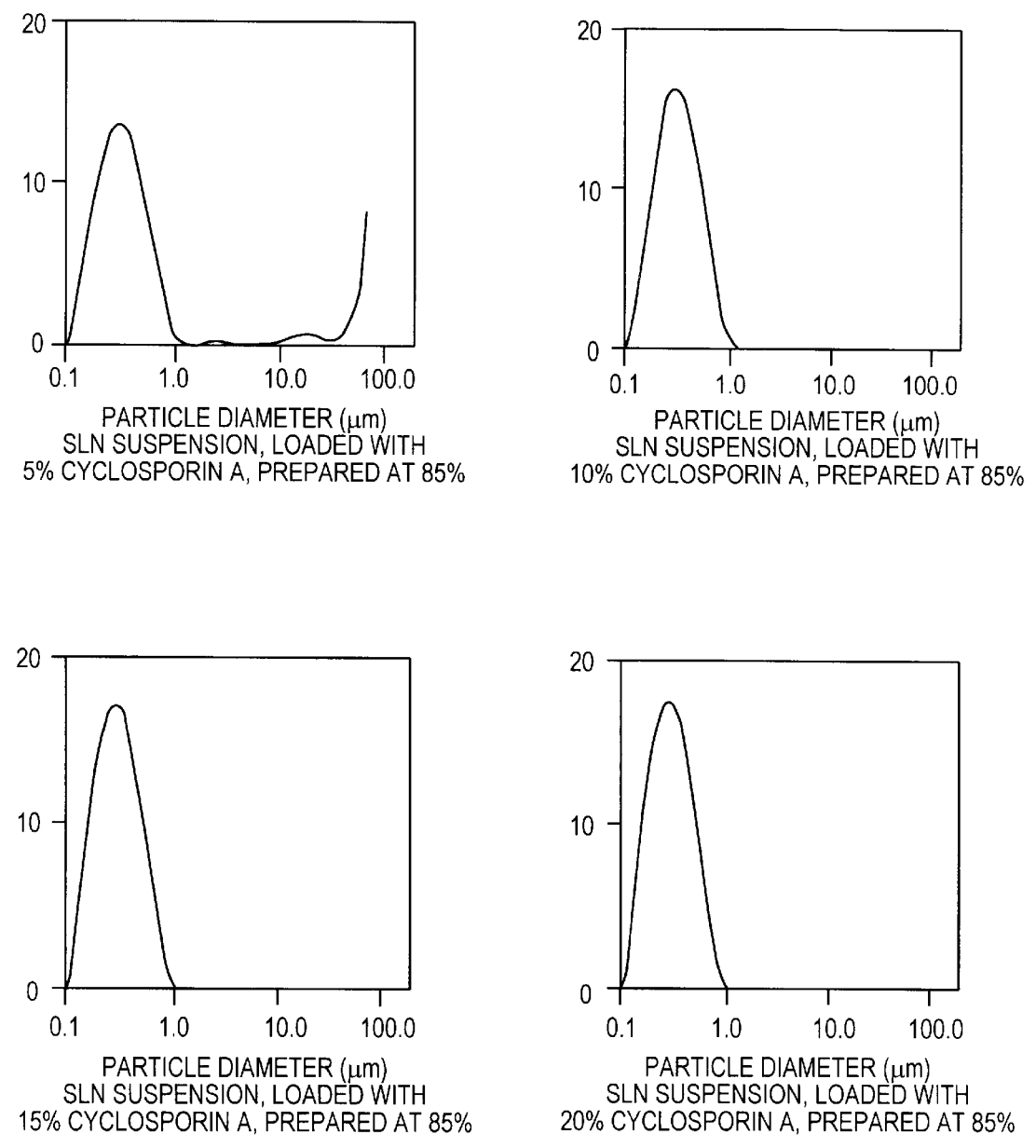

The particle size distribution of formulations with increasing cyclosporin concentrations shown in Table 3 is represented in the graphs in FIG. 4a (hot homogenisation at 85° C.) and FIG. 4b (cold homogenisation at 55° C.). The same effect (uniformity increasing with increased cyclosporin concentration within the lipid matrix) was observed with use of the cold homogenisation technique (example 3, Table 4).

The encapsulation ratio of the drug in the lipid particles is determined by solubility in matrix $C_O$ (oil/lipid phase) and in dispersion medium $C_W$ (water), namely on the basis of distribution coefficient k (=$C_O/C_W$). An increasing concentration of drug in the formulation would therefore be expected to produce a constant encapsulation value if one remains below the maximum solubility of the drug in one of the two phases, lipid or water, at the same time. For example, in view of the high temperature and therefore the increased solubility of the drug, supersaturation of the aqueous phase causes the formation of crystals of the drug after cooling of the dispersion (e.g. prednisolone in (A. zur Mühlen, C. Schwarz, W. Mehnert, *Solid lipid nanoparticles (SLN) for controlled drug delivery—drug release and release mechanism*, Eur. J. Pharm. Biopharm., in press 1983]). Conversely, with an increasing drug concentration amounting to between 0.5% and 2.0% based on the total formulation (=5% to 20% of cyclosporin A, calculated as a percentage of the lipid phase), an increase in the relative encapsulation ratio of between 95.4% and 97.8% took place when the hot homogenisation technique at 85° C. was used (example 5, Table 5). After preparation of the lipid dispersion with the cold homogenisation technique, an increase in the relative encapsulation ratio of between 78.5% and 93.9% was obtained (example 6, Table 6). No drug crystals were found in the aqueous phase. The concentration of the drug in the aqueous phase remained below the saturation solubility value of the aqueous phase containing the emulsifier.

The incorporation of cyclosporin, in particular at increasing concentrations, improved the quality of the particles produced, especially the fineness, uniformity and encapsulation ratio of the drug in the lipid matrix. In addition, the physical stability of the drug-loaded formulation during storage increased. "Physical instability" means particle aggregation and, especially in the case of lipid particles, gel formation. Drug-free Imwitor 900 lipid particles presented high polydispersity after preparation, and aggregated considerably during the first 5 days' storage. They formed fairly large aggregates recognisable under the microscope, of sizes between about 0.5 mm and 1 mm. Lipid particles loaded with 20% cyclosporin proved much more stable, even when stored under stress conditions at 40° C. For example, with reference to the volume distribution of the particles, the LD diameter d50% only increased from 0.32 μm to 0.40 μm, and LD diameter d90% from 0.62 μm to 0.84 μm (after 3 days' storage).

Figure 5:
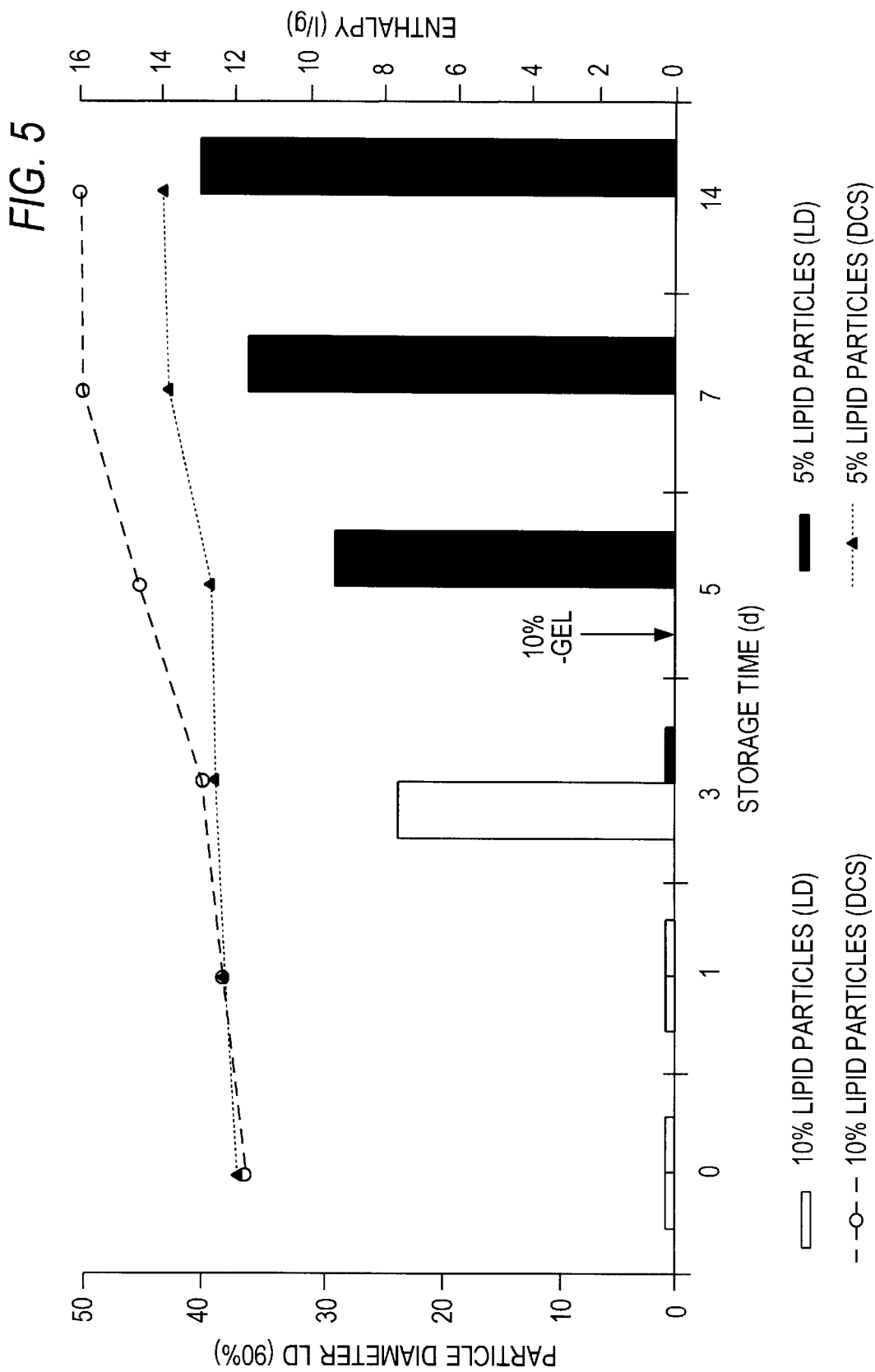
FIG. 5: Increased particle size (laser diffractometry diameter 90%) and increased melting enthalpy on the example of two formulations tending to gel (10% lipids and 5% lipids), represented in relation to storage time and storage conditions (under stress conditions and agitation at 40° C.) [according to: C. Freitas, R. H. Müller, *Long-term stability of solid lipid nanoparticles (SLN™). II. Influence of crystallinity of the lipid and shear forces,* submitted to *Eur. J. Pharm. Biopharm.* 1997]. The particle size was determined by laser diffractometry (Mastersitzer E, Malvern Instruments, England) and DSC (differential scanning calorimetry) analysis using a DSC manufactured by Mettler-Toledo 821e/700, Giessen, Germany. Dimensional analysis of the 10% lipid particle suspensions was only performed on days 0, 1 and 3 after production. The 10% formulation gelled on day 5, creating a creamy consistency which prevented achievement of the particle size analysis.

In earlier experiments with lipid particles it was demonstrated that lipid particles crystallised after preparation, mainly as variant $β'/β_i$ or β, and only partially as the less stable variant α. In the case of physically unstable particles, the proportion of variant β' or $β_i$ increased during storage, while the proportion of variant α decreased, with simultaneous particle aggregation and gel formation. An increase in the melting enthalpy values was also found during particle aggregation, and these values further increased with gel formation [C. Freitas, R. H. Müller, *Long-term stability of solid lipid nanoparticles (SLN™). II. Influence of crystallinity of the lipid and shear forces*, submitted to Eur. J. Pharm. Biopharm. 1997]. FIG. 5 shows the increase in particle size (LD data), gel formation and increase in melting enthalpy (DSC data) of unstable particles.

In the case of physically stable lipid particle dispersions, the proportion of variant β or β' presented little or no change. The proportion of variant α remained unchanged or even increased slightly. Hardly any increase in melting enthalpy was observed.

Cyclosporin aids the formation of variant α with a simultaneous reduction in variant β or β'. This effect becomes increasingly evident as the cyclosporin concentration in the lipid matrix increases (example 4, FIG. 6).

In cyclosporin-loaded lipid particles, only a minimal increase in melting enthalpy was observed, e.g. 9.2 J/g on the first day after preparation, 9.5 J/g on day 14 (20% cyclosporin load in lipid matrix, and storage under stress conditions at 40° C.). These characteristics of lipid particles can be attributed to the addition of cyclosporin, and fully agree with the increased level of physical stability observed as compared to drug-free Imwitor 900 lipid particles.

It is known from suppositories that drugs incorporated into the lipid matrix can be forced to exit the said matrix during storage (drug exclusion) [B. W. Müller, Suppositories, Wissenschaftliche Verlagsgesellschaft Stuttgart, 1989]. This drug exclusion also takes place with dilution of the Sandimmun® oily emulsion concentrate in aqueous dispersion media and causes the formation of large drug crystals in the aqueous phase, or causes the drug to float on the surface of the water. For this reason, the traditional formulation of Sandimmun® is anhydrous in the form of a concentrated oily emulsion. The drug exclusion phenomenon is a problem common to all O/W dispersions, such as other cyclosporin-loaded emulsions [Dietl, H., *Pharmaceutical preparation containing cyclosporin(s) for oral administration and process for producing same*, U.S. Pat. No. 5,637,317, 1997]. The liquid state of the fatty phase in emulsions facilitates drug exclusion, compared to solid suppositories. Drug exclusion is obviously less evident when the oil droplets are very fine, such as those within the lower nanometer range, as in the case of dilution of the Sandimmun Neoral® microemulsion in aqueous dispersion media.

Figure 7:
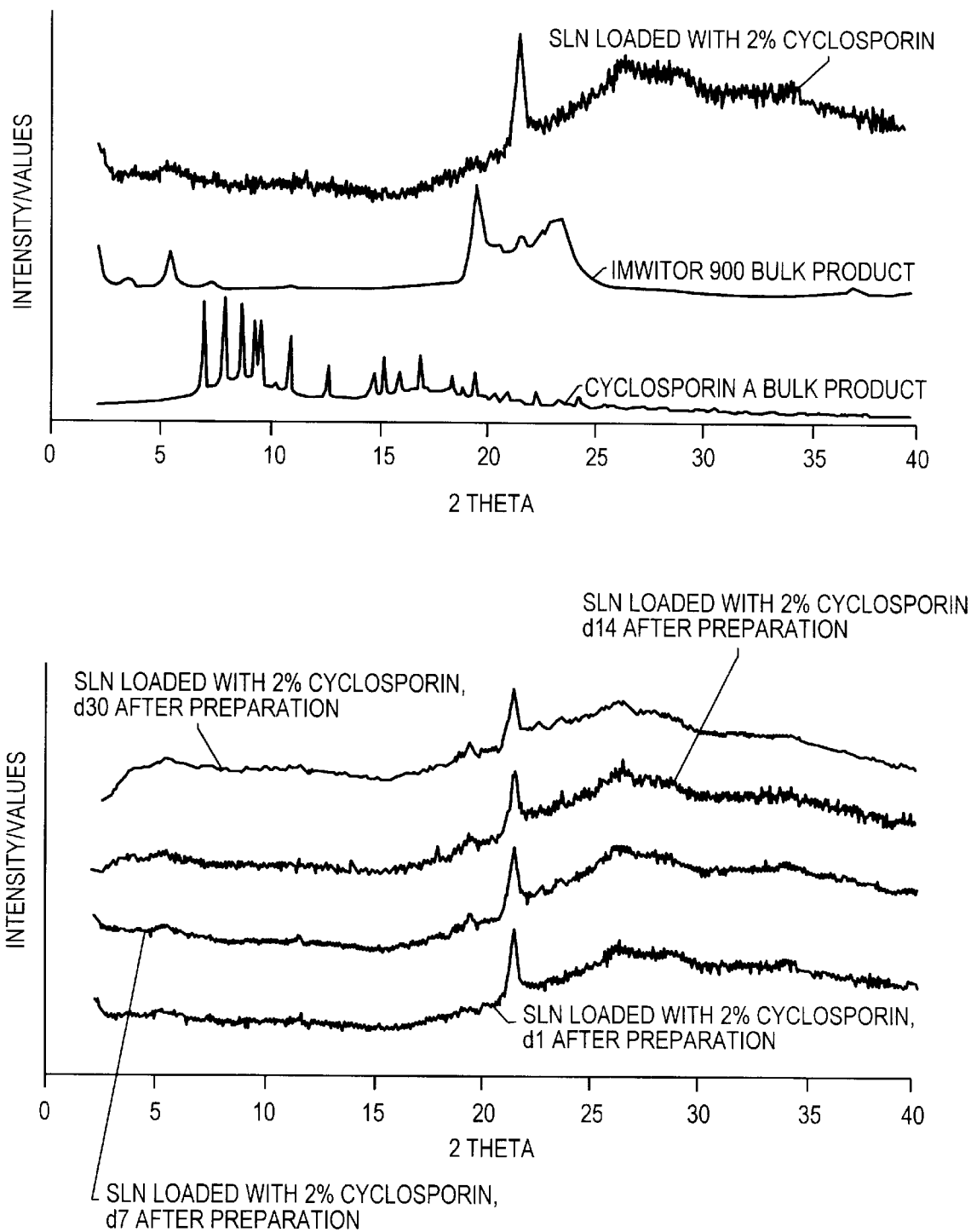
FIG. 7:
   Top: X-ray diffractograms of cyclosporin A and Imwitor 900 bulk material and solid lipid particles loaded with cyclosporin A on day 1 after preparation [2% cyclosporin A, 8% Imwitor 900 (ie. a drug load amounting to 20% of the lipid matrix), 2.5% Tagat® S, 0.5% sodium cholate and 87% water].
   Bottom: X-ray diffractograms of solid lipid particles loaded with cyclosporin A during storage [at 25° C. on days 1, 7, 14 and 30 after preparation (Nonius PDS120 powder diffractometer in simple transmission with irradiation with $Cu_{K\alpha}$)].
Figure 8:
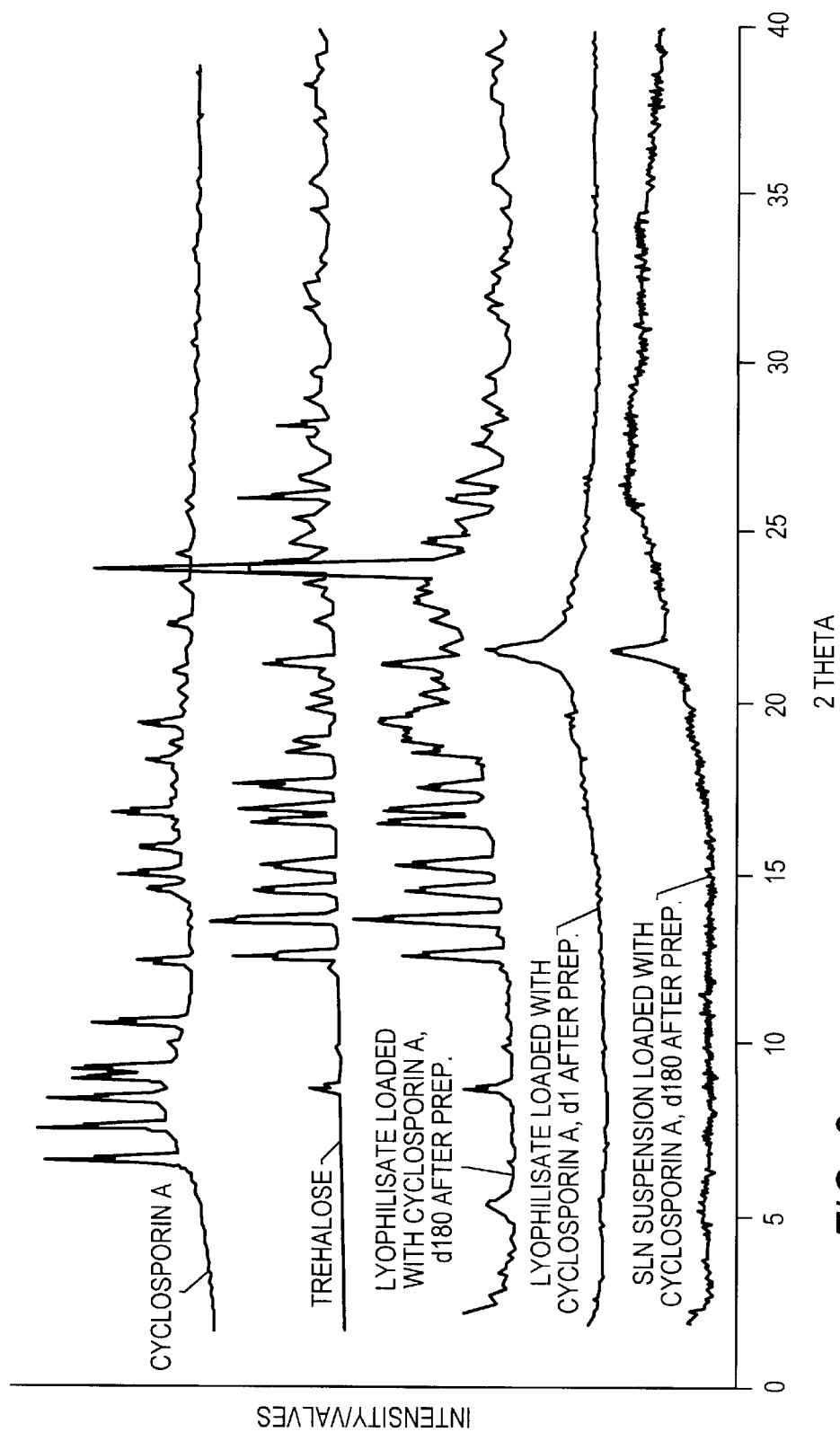
FIG. 8: X-ray diffractograms of solid lipid nanoparticles loaded with 2% cyclosporin A (example 7) on day 1 after preparation (=aqueous suspension), directly after freeze-drying and after 180 days' storage of freeze-dried preparation at 25° C. (Nonius PDS120 powder diffractometer in simple transmission with $Cu_{K\alpha}$ irradiation). The diffractograms of cyclosporin and the cryoprotector trehalose are included as reference.

Departing from these matters of fact, the solid state of the lipid particles and the fineness of the droplets' size represent the main advantages which prevent or at least drastically reduce drug exclusion. The occurence of the crystalline state can be analysed by means of X-ray diffractograms of the aqueous dispersion of solid lipid particles. The diffractograms do not present any variation during 30 days' storage (FIG. 7, bottom). Dry products are generally preferable in view of their long-term stability. Unlike dispersions, they aid the maintenance of physical stability at a reasonable cost. In most countries products with a long shelf life, ie. a minimum physical stability period of 3 years, are required. As a result, the solid lipid particles have been converted into dry products by freeze-drying (example 7) and spray-drying (example 8). X-ray diffractometry analysis of freeze-dried powder after 6 months' storage has demonstrated maintenance of the particles' structure and of the amorphous nature of the cyclosporin incorporated into the lipid matrix. It was impossible to detect cyclosporin crystals, only crystalline diffusion peaks of trehalose, used as cryoprotector of the formulation, became detectable after 180 days' storage (FIG. 8).

Bioavailability: Bioavailability of cyclosporin SLN compared to Sandimmun Neoral after a single oral administration to 9 healthy volunteers. The cyclosporin SLN formulation was prepared as shown in example 1. The material (3 kg) was produced in a Lab 60 APV homogeniser using a pressure of 200 bars, using the continuous process, at 85° C. for 20 mins. The formulation was administered to 9 healthy volunteers in suspension form at a dose of cyclosporin A equivalent to Sandimmun Neoral (300 mg). The mean blood levels are shown in FIG. 9 (top: Sandimmun Neoral; bottom: cyclosporin SLN suspension).

The invention is based on the discovery that the addition of cyclosporin to a lipid matrix increases the dispersity of the lipid, aids the formation of small particles, increases the dimensional uniformity of the particles, increases the encapsulation ratio with the increase in cyclosporin load, increases the physical stability of the particle dispersion during storage, aids the formation of variant α within the lipid matrix and even after storage maintains the structure of the lipid matrix, in particular the proportion of variant α of the lipid and the amorphous nature of the drug incorporated, in particular as a product in dry particle form (e.g. obtained by freeze-drying). A special feature of this invention is therefore the use of cyclosporin in the lipid particle preparation process.

The lipid particles in accordance with the invention are prepared by dispersion of the cyclosporin-loaded lipid phase in its molten form or in the solid state. Different dispersion processes can be used. The technique preferably used is high-pressure homogenisation as described by Müller and Lucks [R. H. Müller and J. S. Lucks, European Patent EP 0 605 497 B1, 1996]. High-pressure homogenisation produces particles with a mean particle diameter, determined by photon correlation spectroscopy (PCS), in the range of between approx. 40 nm and 1000 nm, i.e. so-called solid lipid nanoparticles (SLN®) loaded with cyclosporin. Other dispersing techniques can be used as an alternative to this production technique, such as homogenisation with aid of a microfluidizer (Microfluidics Inc., USA). Larger cyclosporin-loaded particles can be prepared by dispersion of molten or solid fat with aid of a high-speed stirrer or other dispersing devices, as described already by R. H. Müller in application PCT/EP97/06893. Thus, it is possible obtaining matrix-pharmaceutical forms (e.g. tablets or pellets) based on cyclosporin-loaded microparticles. These dispersing devices have a lower power density in the dispersion area and therefore cause the formation of larger lipid particles, e.g. with mean particle diameters of between a few μm and 20 μm or particles between 40 μm and 100 μm, as described in detail in the literature and the standard manuals.

For example, cyclosporin is dissolved or dispersed at high temperature (e.g. between 80 and 90° C.) in the molten lipid phase. Alternatively, cyclosporin can be incorporated into the lipid by precipitation of the lipophilic matrix from a solvent in which lipid and cyclosporin are simultaneously soluble. The lipid matrix may contain cyclosporin in the form of dispersed molecules, in the form of amorphous clusters or in the form of ultrafine crystals (e.g. cyclosporin nanocrystals in lipid particles).

In the case of the hot homogenisation technique, the lipid melt containing cyclosporin is dispersed by stirring in a hot aqueous solution of emulsifier, for example with the use of a stator-rotor system (Ultra-Turax® or Silverson) or with a paddle mixer, a propeller mixer, a toothed disc, etc. Instead of incorporating the emulsifier into the aqueous phase, in the alternative, it can be incorporated into the molten lipid phase. This is particularly advantageous in the case of a lipophilic emulsifier or lecithin. If two or more emulsifiers are used, all the emulsifiers can be dissolved in one phase (aqueous or lipid) or in different phases. The O/W preemulsion obtained is then homogenised by high-pressure homogenisation. For example, a piston-gap homogeniser such as the Micron Lab 40, Lab 60 and/or Gaulin 5.5 (APV-Homogenizer GmbH, Lubeck, Germany) could be used with a typical pressure of between 100 and 1500 bars in one or more homogenisation cycles. The nanoemulsion obtained is cooled and the oily phase solidified, with the formation of cyclosporin-loaded solid nanoparticles (SLN).

If the cold homogenisation technique is used, the melt containing the drug is cooled. The emulsifiers are used as described for the hot homogenisation technique. The solidified fat is ground, for example, in a mortar grinder to obtain a coarse powder. If necessary, dry ice or liquid nitrogen can be added to increase the fragility of the lipid during the grinding process. The ground lipid is dispersed in a cold emulsifier solution and the lipid suspension obtained is homogenised in the solid state. The homogenisation temperature is lower than the melting temperature of the lipid. In the event of possible heat development during the production process, a homogenisation temperature much lower than the melting point of the lipid should be used (e.g. by counter-cooling) to prevent the lipid from melting during the homogenisation process. In high-pressure homogenisation, the temperature is usually at least 5° C. less than the melting point of the fat. In most cases cold homogenisation is performed at ambient temperature; cooling to below ambient temperature is also possible.

Lipids in the widest sense of the term can be used for the dispersed phase as individual active principles or mixtures.

Examples of such lipids are natural or synthetic triglycerides or mixtures thereof, monoglycerides and diglycerides, alone or mixtures thereof or, for example, with triglycerides, self-emulsifying modified lipids, natural and synthetic waxes, fatty alcohols, including their esters and ethers and in the form of lipid peptides, or any mixture thereof. Synthetic monoglycerides, diglycerides and triglycerides as single substances or mixtures (e.g. hard fat), Imwitor 900, triglycerides (such as glycerol trilaurate, glycerol myristate, glycerol palmitate, glycerol stearate and glycerol behenate) and waxes such as cetyl palmitate and white wax (DAB) are particularly suitable.

The internal or lipid part of the phase amounts to between 0.1% and 40% (m/m), and preferably between 1% and 20% (m/m), of the total formulation. If the addition of dispersion-stabilising additives such as emulsifiers is necessary or desired to obtain stable emulsions, they can be incorporated in the form of pure substances or mixtures to stabilise the particles. The quantity of such additives, which can be added on the basis of the initial weight of the aqueous dispersion, lies in the range between 0.01% and 20%, and preferably in the range between 0.5% and 10%.

The following substances can be used as stabilising additives:

1. Surfactants, in particular ethoxylated esters of sorbitan fatty acids, block polymers and block copolymers (such as poloxamers and poloxamines), polyglycerol ethers and polyglycerol esters, lecithins of various origins (such as egg lecithin or soya lecithin), chemically modified lecithins (such as hydrogenated lecithins), as well as phospholipids and sphingolipids, mixtures of lecithins with phospholipids, sterols (such as cholesterol and its derivatives, specifically stigmasterol), esters and ethers of sugars or of sugar alcohols with fatty acids or fatty alcohols (such as saccharose monostearate),
2. sterically stabilising substances such as poloxamers and poloxamines (block copolymers of polyoxyethylene and polyoxypropylene), ethoxylated esters of sorbitan fatty acids, in particular polysorbates (such as polysorbate 80 or Tween 80®), ethoxylated mono- and diglycerides, ethoxylated lipids, ethoxylated fatty alcohols or fatty acids, and
3. charged ionic stabilisers and peptising agents, such as diacetyl phosphates, phosphatidyl glycerol, as well as saturated and unsaturated fatty acids, sodium cholate, sodium glycocholate, sodium taurocholate or mixtures thereof, aminoacids or peptising agents such as sodium citrate (J. S. Lucks, B. W. Müller, R. H. Müller, *Int. J. Pharmaceutics* 63, 183–188, 1990].
4. Viscosity-increasing substances such as cellulose ethers and cellulose esters (e.g. methyl cellulose, hydroxyethylcellulose, hydroxypropylcellulose, sodium carboxymethylcellulose), polyvinyl derivatives are polyvinyl alcohol, polyvinyl pyrrolidone, polyvinyl acetate, alginates, polyacrylates (such as Carbopol®), xanthanes and pectins.

Charge stabilisers, if necessary or desired, are preferably added in the amount of 0.01% to 10% (m/m), and in particular between 0.05% and 2%, of the basic formulation.

Viscosity-increasing agents, if necessary or desired, are incorporated in a comparable ratio preferably in the amount of 0.01–10%, especially in the amount of between 0.1% and 10% (m/m), and preferably between 0.5% and 5% of the basic formulation.

As external phase (=dispersion medium, continuous phase) it is possible to use water, aqueous solutions or liquids miscible with water, such as pure glycerol or polyethylene glycol. Aqueous solutions can be non-isotonic or isotonic for this purpose. Aqueous solutions are mixtures of water with one or more active principles such as glycerol, mannose, glucose, fructose, xylose, trehalose, mannitol, sorbitol, xylitol or other polyols, as well as polyethylene glycols or electrolytes such as sodium chloride. These active principles are added in the amount of between 0.1% by weight and 50% by weight of the basic formulation, and preferably in the amount of between 1% by weight and 30% by weight of the total formulation.

Surfactant-free SLNs are produced by dispersing the lipid phase in an aqueous solution containing one or more viscosity-increasing agents, alone or in combination with other substances, as well as sugars, sugar alcohols, in particular glucose, mannose, trehalose, mannitol, sorbitol and the like. It is also possible to use a combination of viscosity-increasing agents or a combination of those agents with sugars or sugar alcohols or within a further combination with charge stabilisers or peptising agents. Suitable peptising agents might be sodium citrate, sodium pyrophosphate and sodium sorbate, for example.

Cyclosporin can be incorporated into the lipid matrix in various ways:

1. by dissolving the cyclosporin within the internal phase,
2. by dissolving the cyclosporin in a solvent miscible with the internal phase and adding it to the said phase. If necessary, the solvent is subsequently wholly or partially removed,
3. by dispersing the cyclosporin within the lipid phase (for example by dispersing finely-ground cyclosporin (such as cyclosporin crystals of nanometric size) or by controlled precipitation of cyclosporin in the lipid or lipid-solvent mixture)
4. by dissolving cyclosporin in an external aqueous-phase and incorporating the active substance during the production process within a particle-stabilising surfactant film
5. by adsorption of cyclosporin on the particle surface (release tests conducted demonstrate rapid release up to 20%, which indicates that at least part of the drug was located on the surface),
6. by dissolving cyclosporin in the lipid phase with the aid of a solubility-enhancing additive (e.g. a block copolymer or a sorbitan ester of fatty acid) and subsequently dispersing the lipid phase to obtain a pre-emulsion or pre-suspension. Cyclosporin then presents in the lipid matrix in the form of a solid solution.

Sterilisation can be performed as specified in the pharmacopoeia, for example by autoclaving at 110° C. or irradiating with γ-rays, or with other recognised procedures. Another possible sterilisation technique is Tyndallisation.

For oral use, the cyclosporin-loaded SLN dispersions can be transformed into a dry product. The powders can be produced, for example, by spray drying or freeze-drying. The final form is a sachet containing a powder or a soft gelatin capsule. Alternatively, the powder can be processed to make pellets or tablets. Tablets and pellets can be prepared without the intermediate dry powder stage if the SLN dispersion is used in the production of tablets as granulation fluid or to slurry the pellet mass instead of water.

For pulmonary use, the SLN dispersion can nebulised in a nebuliser available on the market (e.g. Pariboy in Germany) and inhaled directly. Alternatively, the SLN powder can be incorporated into a powder inhaler or into other inhalers available on the market.

To prepare ointments or creams with cyclosporin-loaded SLN, an available ointment or cream can be mixed with a concentrated dispersion of SLN (e.g. 20–30%) by stirring. Alternatively, during production, part of the water of the cream can be replaced with an aqueous dispersion of SLN. The cream can also be prepared at higher temperatures than the melting point of the SLNs, as they are sufficiently physically stable. If the SLNs are sufficiently stabilised, no coalescence with oil droplets of the cream will take place. Similarly, in the case of the ointment, part of the oil is replaced with an oily dispersion of SLN.

For the preparation of gels or lotions, the external phase of SLN is formed with a gel former (e.g. aerosil, cellulose derivatives like methyl- and hydroxyethylcellulose, such as Tylose H300 (hydroxypropylcellulose with a polymerisation level of 400 and a molecular weight of 100,000)).

EXAMPLE 1

The cyclosporin A-loaded lipid particles were prepared by dissolving the drug and Tagat® S within the molten Imwitor 900 lipid matrix at 85° C. The hot melt was dispersed with a rotor-stator agitator in an aqueous solution of sodium cholate at 85° C., and the pre-emulsion obtained was homogenised with a LAB 40 microniser (APV Homogenizer GmbH, Lubeck, Germany). High-pressure homogenisation was performed in 3 cycles at 500 bars at 85° C. The formulation contained 8% Imwitor 900, 2% cyclosporin A (or 20% cyclosporin based on the lipid matrix), 2.5 Tagat® S, 0.5% sodium cholate and 87% distilled water.

This formulation was administered orally at the dose of 16 mg/kg to three pigs. The preparation was administered through a stomach catheter after dilution of the SLN dispersion with water to 40 ml; the catheter was then rinsed with 200 ml of water. The pigs were fed 4 hrs after oral administration. The blood level curves were traced as a function of time, and the cyclosporin content was determined by validated enzyme-multiplied immunoassay technique (EMIT). By way of comparison, Sandimmun Neoral® (Novartis Pharma AG, Basle, Switzerland) was used at the same dose and under the same conditions (dilution to 40 ml, oral administration through stomach catheter and rinsing of the catheter with 200 ml of water). The mean blood level of the 3 animals for each of the two preparations are set out in FIG. 2. (top: Sandimmun Neoral® as reference drug; bottom: solid lipid nanoparticles loaded with cyclosporin A).

EXAMPLE 2

Dispersions of solid lipid nanoparticles (SLN) with increasing loads of cyclosporin (5%, 10%, 15% and 20%) were prepared by the hot homogenisation technique. Production was effected by melting the lipid phase at 85%C, dissolving the drug and Tagat® S within the melt by stirring, adding the drug-loaded melt to an aqueous solution of sodium cholate, and preparing a pre-emulsion by stirring with a rotor-stator (Ultra Turrax® T 25, including dispersing unit N 18 G, Jahnke & Kunkel, Stauffen, Germany). The pre-emulsion was homogenised in three homogenisation cycles at 85° C. with a Micron LAB 40 piston-gap homogeniser at controlled temperature (APV Homogenizer GmbH, Lubeck, Germany) at 500 bars. The composition of the SLN formulations is set out in Table 2.

Table 2: Composition of SLN formulations loaded with increasing proportions of cyclosporin A. The percentages of cyclosporin are calculated as percentages of the total formulation and as percentages of the lipid matrix (*) The lipid matrix (Imwitor 90 and cyclosporin A) remains constant at 10% of the total formulation.

| Imwitor 900 | Cyclosporin A | Tagat ® S | Sodium cholate | Demin. water |
|---|---|---|---|---|
| Imwitor 900 SLN suspension loaded with 5% cyclosporin ||||| 
| 9.5% | 0.5% (−5%*) | 2.5% | 0.5% | to 100% |
| Imwitor 900 SLN suspension loaded with 10% cyclosporin |||||
| 9.0% | 1.0% (−10%*) | 2.5% | 0.5% | to 100% |
| Imwitor 900 SLN suspension loaded with 15% cyclosporin |||||
| 8.5% | 1.5% (−15%*) | 2.5% | 0.5% | to 100% |
| Imwitor 900 SLN suspension loaded with 20% cyclosporin |||||
| 8.0% | 2.0% (−20%*) | 2.5% | 0.5% | to 100% |

The particle sizes were determined by laser diffractometry (LD) with a Mastersizer E (Malvern Instruments, UK). The LD diameters d50%, d95% and d99% were chosen to determine and characterise the fineness of the particle dispersions. The particle size values are listed in Table 3; whereas the size distribution curves are shown in FIG. 4a.

Table 3: Diameters (LD) D50%, D95% and D99% of the cyclosporin-loaded SLN formulations shown in Table 2, prepared by hot homogenisation (mean particle diameter of n=3) (laser diffractometry data, volume distribution).

|  | d50% [μm] | d95% [μm] | d99% [μm] |
|---|---|---|---|
| 5% drug load | 0.40 | 34.58 | 60.62 |
| 10% drug load | 0.34 | 0.81 | 5.68 |
| 15% drug load | 0.32 | 0.70 | 1.24 |
| 20% drug load | 0.31 | 0.69 | 0.86 |

EXAMPLE 3

Dispersions of solid lipid nanoparticles (SLN) with increasing loads of cyclosporin A (5%, 10%, 15% and 20%) were prepared with identical composition as described in example 2 (Table 2), but with the use of the cold homogenisation technique. After dissolution of the drug and Tagat® S within the lipid melt, the said melt was cooled and ground in a mortar grinder (Mörsermühle, Retsch, Hahn, Germany) for 10 min. The coarse particles obtained were dispersed in an aqueous solution of sodium cholate with an Ultra Turrax®. The suspension obtained was homogenised at 55° C., i.e. about 5° C. below the melting range of Imwitor 900 (melting range between 59° C. and 61° C.). A Micron Lab 40 (APV Homogenizer GmbH, Lubeck, Germany) was used at controlled temperature, and homogenisation was performed in 3 homogenisation cycles at ambient temperature. The particle size was determined by laser diffractometry (LD) (Mastersizer E, Malvern Instruments, UK). LD diameters d50%, d95% and d99%, were chosen to characterise the fineness of the particles in the dispersion and are set out in able 4, whereas the corresponding size distribution curves are shown in FIG. 4b.

Table 4: LD Diameters d50%, d95% and d99% of the drug-loaded SLN formulations shown in Table 2, produced by cold homogenisation (mean particle diameter of n=2) (laser diffractometry data, volume distribution).

|  | d50% [μm] | d95% [μm] | d99% [μm] |
|---|---|---|---|
| 5% drug load | 0.69 | 37.58 | 71.80 |
| 10% drug load | 0.49 | 10.37 | 51.90 |
| 15% drug load | 0.46 | 10.53 | 23.93 |
| 20% drug load | 0.59 | 10.82 | 24.43 |

EXAMPLE 4

Figure 6:
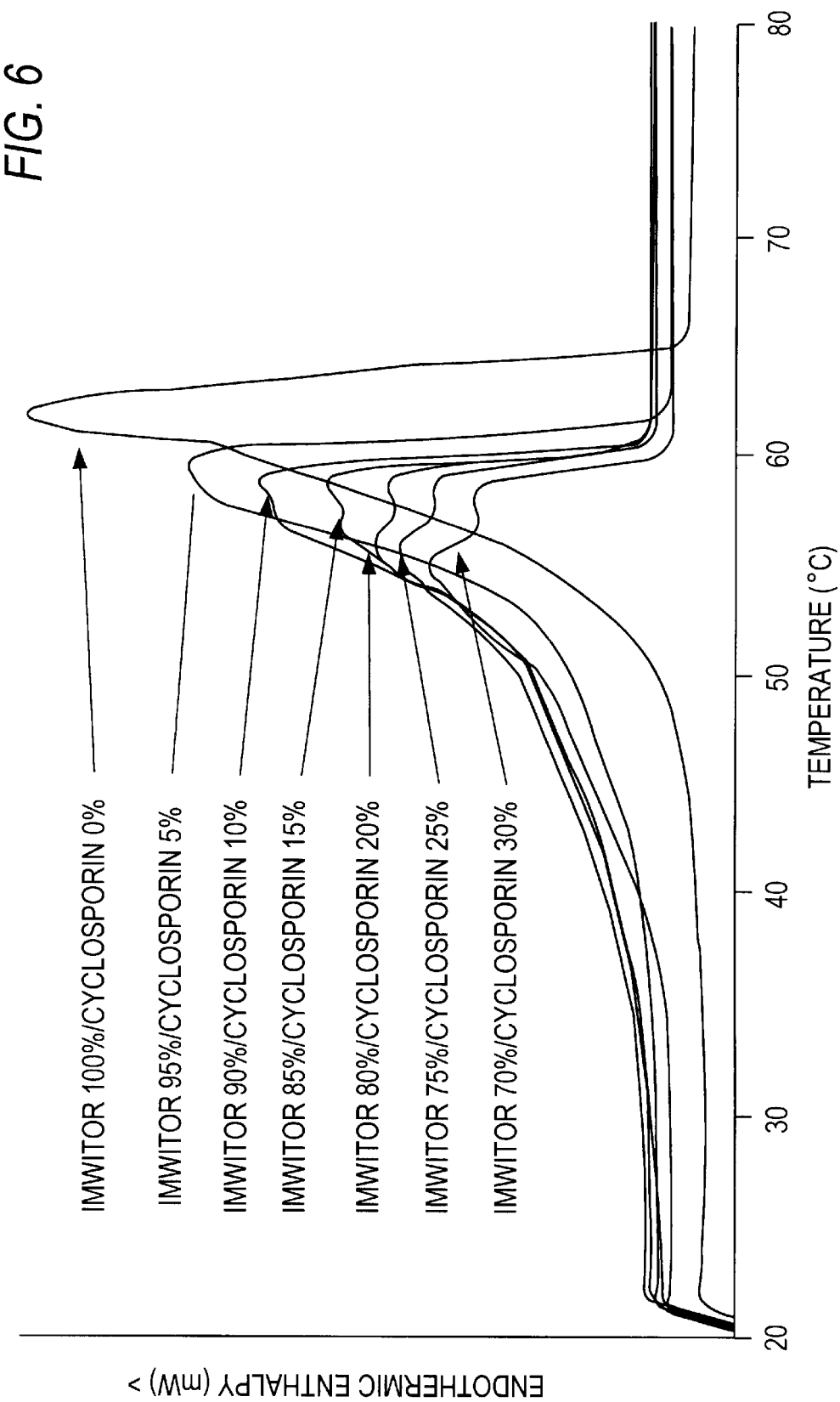
FIG. 6: DSC heating curves of Imwitor 900 bulk material and Imwitor 900 lipid matrixes with an increasing concentration of dissolved drug (cyclosporin A) ranging from 5 to 30%. The DSC heating curves were measured after dissolution of the drug in the Imwitor 900 matrix at 85° C. for 15 mins., and crystallisation of the mixture for one hour at ambient temperature. The heating rate was 5 kelvins/min.; a Mettler-Toledo 821E/700 DSC was used (Mettler-Toledo, Giessen, Germany).

Physical lipid-drug mixtures of Imwitor 900 and cyclosporin A were prepared with a cyclosporin A content increasing from 0% to 30%. Cyclosporin A was dissolved in Imwitor 900 by heating for 15 min. at 85° C., then the lipid matrix with the drug dissolved and incorporated therein was cooled down again. The DSC heating curves of the mixtures thus obtained present an increase in the less stable fraction of variant α (FIG. 6).

EXAMPLE 5

The encapsulation ratio was determined by HPLC analysis; in this case the SLN particles were loaded with an increasing cyclosporin A content. The particles were prepared by the hot homogenisation technique in 3 homogenisation cycles, at 500 bars at 85° C. (composition: see Table 2). The encapsulation ratio is defined as the percentage of the total drug concentration within the formulation which is incorporated within the particles (100% of the drug in the formulation corresponds to X percent in the lipid particle plus Y percent of free drug in the aqueous phase). The data are listed in Table 5.

Table 5: Encapsulation ratios with increasing load of cyclosporin A; particles prepared by the hot homogenisation technique at 85° C. (mean value of n=3).

|  | Encapsulation ratio |
| --- | --- |
| 5% drug load | 95.4% |
| 10% drug load | 96.5% |
| 15% drug load | 97.5% |
| 20% drug load | 97.8% |

EXAMPLE 6

The encapsulation ratio was determined by HPLC analysis of SLN particles with increasing percentages of drug in the lipid matrix; the particles were prepared with the cold homogenisation technique in 3 cycles at 55° C. (composition: see Table 2). The data are listed in Table 6.

Table 6: Encapsulation values with an increasing load of cyclosporin; particles prepared by the cold homogenisation technique at 55° C.

|  | Encapsulation ratio |
| --- | --- |
| 5% drug load | 78.5% |
| 10% drug load | 89.7% |
| 15% drug load | 92.0% |
| 20% drug load | 93.9% |

EXAMPLE 7

An aqueous solution consisting of 10% trehalose (m/m) was mixed and freeze-dried in a 1:1 ratio with an aqueous dispersion of solid lipid particles (8% Imwitor 900, 2% cyclosporin A, 2.5% Tagat® S, 0.5% sodium cholate and 87% distilled water). The freezing process was performed at −20° C. in bottles for injection with 2 ml of trehalose/lipid particle mixture. Freeze-drying was performed in a Gamma-2-20 unit (Christ, Osterode i.H., Germany), for 24 hrs at −10° C. with a vacuum of 0.370 bars. The suspension was subsequently re-dried at 0° C., 370 mbars for 12 hrs. The product was a dry powder in flakes; the cyclosporin was encapsulated within the lipid matrix in an amorphous state, as detectable by broad-angle X-ray diffractometry. The X-ray structural analysis of the product was conducted on day 1 after freeze-drying and on day 180 after storage at 25° C. (FIG. 8).

After 180 days' storage, only crystallisation of trehalose was observed, as clearly recognisable from the dispersion peaks in the angle range 2 Theta=13° and above. The cyclosporin remained in an amorphous state throughout the whole storage period, which is clearly recognisable by the absence of characteristic cyclosporin crystalline peaks in the diffraction pattern shown in FIG. 8 (2 Theta=7° to 13°).

EXAMPLE 8

The amount of 10% trehalose (m/m) in an aqueous solution of 10% ethanol was mixed in a 1:1 ratio with an aqueous dispersion of solid lipid particles (8% Imwitor 900, 2% cyclosporin A, 2.5% Tagat® S, 0.5% sodium cholate and 87% distilled water). The mixture obtained was spray-dried with a Minibtichi (Büichi, Switzerland). The spray-drying parameters were as follows: inlet temperature 95° C., outlet temperature 45° C., flow rate 1 ml/min. The product was a dry powder in flakes. The cyclosporin was encapsulated within the lipid matrix in an amorphous form.

EXAMPLE 9

2 kg preparations of SLN dispersion were produced with a modified Lab 60 piston-gap homogeniser (APV Homogenizer GmbH, Lubeck, Germany). The homogeniser was provided with coolable containers, tubes and homogenising valves as described in [R. H. Müller, S. Gohla, G. E. Hildebrand, S. A. Runge, A. Dingler, *Dispersion of solid lipids—solid lipid nanoparticles (SLN)*: *Production and possible applications in food, cosmetics and pharmaceutical products,* World Congress on Emulsion, Bordeaux, 1-2-195, 1997]. The 10 kg feed container was fitted with a toothed disc, and the product collection container with a stainless steel propeller agitator having 4 paddles. Production was carried out in the continuous loop modus, i.e. after the passage of the homogenising gap and after completion of homogenisation, the finely dispersed product was returned directly to the feed container for repeated homogenisation.

40.0 g of cyclosporin A (2.0%) was dissolved under agitation at 85° C. in 160.0 g of molten Imwitor 900 (8.0%) with 50.0 g of Tagat® S (2.5%). The 250.0 g of melt was dispersed in 1750 g of water with 10.0 g of sodium cholate (0.5%). Homogenisation was performed in the continuous loop modus for 20 mins. at 85° C., at 500 bars. The formulations were prepared with homogenisation times increasing in 5-minute stages (Table 7). The particle size analysis was performed by laser diffractometry (Mastersizer E, Malvern Instr., UK) and photon correlation spectroscopy (Coulter N4Plus, Coulter Electr., USA).

Table 7: Particle size analysis of a 2-liter preparation of lipid particle dispersions loaded with 2% cyclosporin A, prepared by the hot homogenisation technique with a modified LAB 60 high-pressure piston-gap homogeniser. The preparations were made with increasing homogenisation times (5 min., 10 min., 15 min., and 20 min). Laser diffractometry data (LD diameters d50% and d95%, volume distribution) and photon correlation spectroscopy data (mean PCS particle diameter).

| Preparation | Homogenisation time | Particle size parameters | |
| --- | --- | --- | --- |
| 1 | 5 min. | LD diameter d50% | 0.40 μm |
|  |  | LD diameter d95% | 0.99 μm |
|  |  | PCS diameter | 221 nm |

-continued

| Preparation | Homogenisation time | Particle size parameters | |
|---|---|---|---|
| 2 | 10 min. | LD diameter d50% | 0.33 μm |
|   |         | LD diameter d95% | 0.77 μm |
|   |         | PCS diameter     | 199 nm |
| 3 | 15 min. | LD diameter d50% | 0.31 μm |
|   |         | LD diameter d95% | 0.69 μm |
|   |         | PCS diameter     | 184 nm |
| 4 | 20 min. | LD diameter d50% | 0.31 μm |
|   |         | LD diameter d95% | 0.68 μm |
|   |         | PCS diameter     | 180 nm |

EXAMPLE 10

40.0 g of cyclosporin (=2%) was dissolved under agitation at 80° C. in 160.0 g of molten Imwitor 900 (8.0%) containing 50.0 g of Tagat® S (2.5%). The 250.0 g melt was dispersed in 1750 g of water containing 10.0 g of sodium cholate (0.5%). The emulsion was dispersed with a toothed disc for 1 min. at 150 rpm at 80° C. (Table 8). The particle size analysis was performed by laser diffractometry and photon correlation spectroscopy (Mastersizer E, Malvern Instr., UK for laser diffractometry and Coulter N4Plus, Coulter Electr., USA for photon correlation spectroscopy).

Table 8: Particle size analysis of a 2-liter preparation of a lipid particle dispersion loaded with 2% cyclosporin A after agitation with a toothed disc (diam.=15 cm) at 85° C. and at 150 rpm. Laser diffractometry data (LD diameters d50% and d95%, volume distribution), photon correlation spectroscopy data (mean PCS particle diameter).

| LD diameter d50% | 0.83 μm |
|---|---|
| LD diameter d95% | 19.33 μm |
| PCS diameter | 322 nm |

EXAMPLE 11

800 mg cyclosporin was dissolved under agitation at the temperature of 85° C. in 3200 mg of molten Compritol 888 ATO. The melt (4.0 g) was dispersed in 36.0 g of water. The aqueous solution contained polysorbate 80 and soya lecithin (Lipoid S75). The emulsifier concentration was 1360 mg or 120 mg (calculated as a proportion of the total formulation of 40.0 g, corresponding to 3.4% polysorbate 80 and 0.3% Lipoid S 75). The lipid dispersion was homogenised at 85° C. by hot homogenisation at apressure of 500 bars with 3 homogenising cycles (Table 9). The particle size analysis was performed by laser diffractometry and photon correlation spectroscopy (Mastersizer E, Malvern Instruments, UK for laser diffractometry and Coulter N4Plus, Coulter Electronics, USA for photon correlation spectroscopy).

Table 9: Particle size analysis of a dispersion of lipid particles loaded with 2% cyclosporin with Compritol 888 ATO as lipid matrix (8%), and cyclosporin (2%), polysorbate 80 (3.4%) and soya lecithin (Lipoid S 75, 0.3%) as emulsifiers in distilled water (86.3%). Laser diffractometry data (d50%, d95% and d99%, volume distribution), photon correlation spectroscopy data (mean PCS particle diameter, polydispersity index (PI)).

| LD diameter d50% | 0.33 μm |
|---|---|
| LD diameter d95% | 0.91 μm |
| LD diameter d99% | 3.00 μm |
| PCS diameter | 163 nm |
| PCS polydispersity index | 0.339 |

EXAMPLE 12

800 mg cyclosporin was dissolved under agitation at 85° C. in 3200 mg of molten Precirol ATO 5 as lipid matrix. The 4.0 g melt was dispersed in 36.0 g of water with Poloxamer 188 and sodium cholate (calculated as a proportion of the total 40.0 g formulation corresponding to 2.5% Poloxamer 188 and 0.5% sodium cholate) as emulsifiers. Hot homogenisation and particle size analysis (Table 10) were performed as specified in example 11.

Table 10: Particle size analysis of a dispersion of lipid particles loaded with 2% cyclosporin with Precirol ATOS as lipid matrix (8%), cyclosporin (2%), Poloxamer 188 (2.5%) and sodium cholate (0.5%) as emulsifiers in distilled water (87%). Laser diffractometry data (d50%, d95% and d99%, volume distribution), photon correlation spectroscopy data (mean PCS particle diameter, polydispersity index (PI)).

| LD diameter d50% | 0.30 μm |
|---|---|
| LD diameter d95% | 0.74 μm |
| LD diameter d99% | 5.73 μm |
| PCS diameter | 193 nm |
| PCS polydispersity index | 0.312 |

EXAMPLE 13

800 mg of cyclosporin was dissolved under agitation at 85° C. in 3200 mg of molten beeswax; the 4.0 g melt was dispersed in 36.0 g of water with polysorbate 80 as emulsifier. The emulsifier concentration was 480 mg (calculated on the basis of the total 40.0 g formulation and corresponding to 1.2%). Hot homogenisation and particle size analysis (Table 11) were performed as shown in example 11.

Table 11: Particle size analysis of a dispersion of lipid particles loaded with 2% cyclosporin with beeswax as lipid matrix (8%), and cyclosporin (2%) and polysorbate 80 (1.2%) as emulsifier in distilled water (88.8%). Laser diffractometry data (d50%, d95% and d99%, volume distribution), photon correlation spectroscopy data (mean PCS particle diameter, polydispersity index (PI)).

| LD Diameter d50% | 0.36 μm |
|---|---|
| LD Diameter d95% | 1.20 μm |
| LD Diameter d99% | 3.51 μm |
| PCS Diameter | 279 nm |
| PCS polydispersity index | 0.148 |

EXAMPLE 14

Preparation of SLN with Tetracaine

For the preparation of lipid particles loaded with tetracaine, 0.40 g of tetracaine was dissolved in 3.60 g of molten Imwitor 900 (=10% of drug within lipid phase). 1.00 g of Tagat S was added to the melt, and the said melt was then dispersed with a rotor-stator in 35.0 g of hot water to which 0.20 g of sodium cholate had been added. The total formulation therefore contained 10% lipid phase (9% lipid and 1% tetracaine), 2.5% Tagat S, 0.5% sodium cholate and 87% water. The raw emulsion obtained was homogenised with a LAB40 at 85° C. and at a pressure of 500 bars in 3 cycles. Solid lipid particles formed after cooling. The result of the particle size analysis by laser diffractometer (MasterSizer E, Malvern Instruments) was a 50% diameter of 0.39 µm, a 95% diameter of 65 µm and a 99% diameter of 77 µm.

For the preparation of lipid particles loaded with tetracaine with 20% of drug in the lipid phase, 0.80 g of tetracaine was dissolved in 3.20 g of molten Imwitor 900, and the process described above was performed. The result of the particle size analysis was a 50% diameter of 0.44 µm, a 95% diameter of 71 µm and a 99% diameter of 78 µm. When the drug content was increased, the polydispersity also increased.

For the preparation of lipid particles loaded with tetracaine with the use of Compritol as lipid, the same process was performed as for the production of tetracaine-loaded Imwitor 900 particles. A 10% drug content in the lipid phase produced a 50% diameter of 0.45 µm, a 95% diameter of 75 µm and a 99% diameter of 79 µm.

A 20% drug content in the lipid phase produced a 50% diameter of 0.39 µm, a 95% diameter of 73 µm, and a 99% diameter of 79 µm.

The replacement of cyclosporin with tetracaine led to extreme polydispersity of the particles. With 10% drug in the lipid phase, 95% of the particles fell into a broad range of 0.1–65 or 75 µm with Imwitor 900 or Compritol as lipid (compare to cyclosporin in example 2: 0.1–0.8 µm.).

An increase in the drug proportion did not improve homogeneity, as observed, for example, for cyclosporin-loaded particles; likewise the 99% diameter remained unchanged at approx. 78 µm (compare to cyclosporin in example 2; when the cyclosporin was increased from 10% to 20%, the 99% diameter reduced from 5.68 Mm to 0.86 µm).
Problems Involved in Cyclosporin Treatment and the Necessary Drug Monitoring Determination of the pharmacokinetics of cyclosporin depends on the type of biological medium used (blood vs. plasma or serum) and on the method used for the test (radioimmunoassay (RIA) vs. high-pressure liquid chromatography (HPLC)). In view of this dependence, it is very difficult to interpret the pharmacokinetic data and establish a correlation between the concentration in biological fluids and the therapeutic and/or toxic effects of this drug. The most frequent side effect of cyclosporin which is most important in clinical practice is dose-dependent nephrotoxicity. Higher cyclosporin levels in the blood lead to higher concentrations of the drug in the kidneys, which cause a series of histological changes of various kinds. In view of this frequent complication, cyclosporin treatment requires individual doses to be established by means of expensive, lengthy monitoring of the blood levels and kidney function. Hospital physicians perform regular monitoring, daily or 3/4 times a week during the first post-transplant period, following which monitoring is reduced to once a month between 6 months and 1 year after the transplant. Monitoring generally focuses on the Trough blood level, ie. the tailing blood level after the first plasma peak (e.g. in 24 hours).
Dosage, Blood Levels, Therapeutic Efficacy and Toxicity of Cyclosporin The maximum level concentrations (peaks) of cyclosporin in the blood (determined by HPLC) correspond to approx. 1.4–2.7 ng/ml per 1 mg of peroral dose of a conventional formulation (such as Sandimmun) administered to healthy adult volunteers. The cyclosporin emulsion formulation (Sandimmun Neoral/Optoral) presents higher bioavailability, which causes higher blood level peaks and a larger area under the drug/time concentration curve (AUC).

Trough blood concentrations measured by RIA (after 24 hrs) equal to 250–800 ng/ml seem to minimise both, frequency of organ rejection and the side effects of cyclosporin. A correlation has been observed between Trough concentrations in the serum (measured by RIA) exceeding 500 ng/ml (corresponding blood concentration range 700–1350 ng/ml) and cyclosporin-induced nephrotoxicity.

Table 12 summarises the human clinical data and illustrates the effect of dose on maximum blood concentration (determined by RIA) (AHFS data, American Hospital Formulary Service, 1997, pp. 2862–2873). For comparison purposes and to demonstrate the effect of the invention, the findings of a study on pigs are enclosed.

EXAMPLE 15

Lipid particles loaded with cyclosporin A were prepared as specified in example 1. The formulation contained 16% Imwitor 900, 4% cyclosporin A, 2.5% Tagat S, 0.5% sodium cholate and 77% water (ie. 20% lipid particles in the dispersion). 20 parts of the lipid particle dispersion were gradually incorporated under agitation into 80 parts of basic cream (Deutscher Arzneimittel-Codex (DAC), 1979, Govi-Verlag GmbH, Frankfurt/Main, Germany). The incorporation was performed with an mortar and pestle at ambient temperature. The cream contained a proportion of 4% of cyclosporin-loaded lipid particles.

EXAMPLE 16

Lipid particles loaded with cyclosporin A were prepared as described in example 12. 1.0 g of Tylose H300 (hydroxyethylcellulose, polymerisation level 400, molecular weight 100,000) and 10.0 g of glycerol (87% in water) were added to 100 g of aqueous dispersion of lipid particles. The Tylose H300 was mixed with the glycerol with mortar and pestle. After fine distribution of the Tylose H300 in glycerol, the lipid particle dispersion was gradually added. After a period of swelling, a gel formed.

EXAMPLE 17

Lipid particles loaded with cyclosporin A were prepared as described in example 12. 100 g of basic cream was prepared as described in the DAC, 10 g of water being replaced with an aqueous dispersion of lipid particles. The cream produced at high temperature, above the melting point of the lipid particles, contains solid lipid particles (melting peak in analysis and differential scanning calorimetry).

EXAMPLE 18

Cyclosporin (0.5%) was dissolved in molten Compritol (4%); the resulting solution was dispersed in Miglyol 812 at 80° C., with the addition of Span 80 (1.2%), with an Ultra-Turrax, then homogenised at high pressure (500 bars, 3 cycles at 80 C.). To prepare an ointment, 0.3 g of Aerosil 200 was mixed with 30 g of lipid particle dispersion after cooling.

Table 12: Dose administered at peak blood concentration (measured by RIA)
Comparison: Findings of Study on Pigs

| Species | Formulation | Dose (mg/kg) | $C_{max}$ (ng/ml) |
|---|---|---|---|
| Adult, new kidney transplant | Neoral | 7.95 (u.i.d.) | 1802 (after 4 weeks) |
| Adult, new liver transplant | Neoral | 6.9 (u.i.d.) | 1555 (after 4 weeks) |
| 7–15 years, stable kidney transplant | Neoral | 3.7 (b.i.d.) | 1827 |
| 3 years, stable liver transplant | Neoral | 4.15 (b.i.d.) | 1050 |
| Pig | Neoral | 16 single doses | 1467.7 |
| Pig | SLN | 16 single doses | 745.7 |

The administration of a mean maintenance dose of cyclosporin (e.g. 8 mg/kg) to an adult patient weighing 70 kg with Trough blood values of 700–1350 ng/ml would result in a maximum blood level concentration (peak) of between 1484 ng/ml and 2863 ng/ml (calculated on the basis of HPLC data for Sandimmun, manufacturer's data). In view of the lower sensitivity of HPLC as compared to RIA and the higher bioavailability of Neoral, even higher peak blood level values for Neoral can be forecast. On the basis of these factors, toxic blood level values of cyclosporin exceeding 1500 ng/l can be assumed. The administration of higher maintenance doses to obtain higher Trough blood values, which are more advantageous in therapeutic terms, would produce high peaks which reach toxic blood levels with the prior art formulations.

Clinical Advantages of the Invention

FIG. 2 and the pharmacokinetic data obtained in the study on pigs demonstrate that the exclusive and surprising characteristic of the invention is a drastic reduction (50%) and slowing of the maximum blood concentrations compared to Neoral at the same intragastric dose. The Trough blood values for the two preparations are similar, and the AUC values are comparable within the range of pharmaceutical bioequivalence limit values. As is well known, the gastrointestinal anatomy of the pig is comparable to the human gastrointestinal anatomy, and the findings of studies on pigs in a commensurate manner reflect the basic situation in man. The maximum blood level concentration, considerably reduced by the formulation in accordance with the invention, and slowing of its appearance, are particularly advantageous for cyclosporin treatment for the following reasons:

1. Significant reduction in risk of nephrotoxicity.
2. Greater flexibility of increased doses in view of the reduction or elimination of plasma peaks
3. The higher dose, for the first time, allows regulation of the highest trough levels in the blood, which reduces rejection reactions (greater therapeutic efficacy).
4. Reduced frequency of the regular monitoring of cyclosporin concentrations in the blood and of regular monitoring of the kidney function which has been necessary to date, and is lengthy and expensive.

These benefits of the formulation in accordance with the invention are particularly advantageous in paediatric treatment with cyclosporin, not only to prevent rejection but also for the treatment of a series of inflammatory diseases which are difficult to treat (such as Crohn's disease, ulcerating colitis, psoriasis and juvenile arthritis) and present a significant prevalence (e.g. over 1 million) in the USA.

What is claimed is:

1. A vehicle for medicinal preparations which comprises solid lipid particles loaded with cyclosporine-A having a particle diameter of between 10 mn and 10 μm, which are prepared by homogenization at high pressure and at room temperature, and which have a mean photo correlation spectroscopy (PCS) particle diameter in the 40 nm to 1,000 nm range.

2. The vehicle for medicinal preparations according to claim 1, wherein particles of a lipid or of a lipid mixture with or without surfactant, are prepared by dispersion of a lipid phase within a dispersing medium in a melted or softened form, or by dispersion of the lipid phase in a solid form within a dispersing medium, in which the solid phase is reduced to fine particles prior to dispersion.

3. The vehicle for medicinal preparations according to claim 2, wherein the particles have a mean particle diameter in the 100 nm to 500 nm range and wherein the mean PCS diameter of the particles is in the 40 nm to 100 nm range.

4. The vehicle for medicinal preparations according to claim 1, comprising an internal lipid phase content, calculated on the total amount of the preparation, is in the 0.1% to 40% (w/w) range.

5. The vehicle for medicinal preparations according to claim 1, wherein a material comprising a matrix of the particles is selected from the group consisting of monoglycerides, diglycerides and/or triglycerides, a fatty alcohol, its esters or ethers, wax or a lipid peptide and mixtures thereof.

6. The vehicle for medicinal preparations according to claim 1 which is selected from the group consisting of glycerol trilaurate, glycerol myristate, glycerol palmitate, glycerol stearate and/or glycerol behenate, or mixtures thereof with monoglycerides, diglycerides and triglycerides, as a mixture of glycerides, fatty alcohols, and/or waxes.

7. The vehicle for medicinal preparations according to claim 1 further containing one or more additives for the stabilization of a dispersion, in an amount, based on the total amount of the formulation, of between 0.1% and 30% (w/w).

8. The vehicle for medicinal preparations according to claim 7, wherein the additives for the stabilization of the dispersion are selected from the group consisting of poloxamers, poloxamines, ethoxylated monoglycerides and diglycerides, ethoxylated lipids, ethoxylated fatty alcohols and alkyl phenols, ethoxylated fatty acid esters, polyglycerin ethers and esters, lecithin, esters and ethers of sugars or sugar alcohols with fatty acids or fatty alcohols, phospholipids and sphingolipids, sterols or their esters and ethers, whether alone or in the form of their mixtures.

9. The vehicle for medicinal preparations according to claim 7, wherein the additives for the stabilization of the dispersion are selected from the group consisting of lecithin of egg, lecithin of soya or hydrated lecithin, and their mixtures, and optionally a mixture of lecithin of soya and/or hydrated lecithin, with one or more phospholipid components, cholesterol, cholesterol palmitate, stigmasterin or other sterols.

10. The vehicle for medicinal preparations according to claim 1, further containing charged ionic stabilizers in an amount, calculated on the original preparation, of between 0.01% and 10% (w/w).

11. The vehicle for medicinal preparations according to claim 10, wherein the charged ionic stabilizer is selected from the group consisting of diacetyl phosphate, phosphatidyl glycerol, saturated or unsaturated fatty acids, sodium cholate, sodium glycocholate, sodium taurocholate or their mixtures and/or amino acids.

12. The vehicle for medicinal preparations according to claim 7 further containing at least one viscosity increasing substance in an amount, calculated based on the original preparation, of between 0.1% and 10% (w/w).

13. The vehicle for medicinal preparations according to claim 12, wherein the viscosity increasing substance is selected from the group consisting of cellulose, its ethers and esters, polyvinyl derivatives, alginates, polyacrylates, xanthans and/or pectins, and mixtures thereof.

14. The vehicle for medicinal preparations according to claim 12 further containing one or more sugars and/or more sugar alcohols, selected from the group consisting of glucose, mannose, trehalose, mannitol and/or sorbitol.

15. The vehicle for medicinal preparations according to claim 12 further containing peptizers.

16. The vehicle for medicinal preparations according to claim 1, wherein the particles are lyophilized or spray-dried or processed or converted into a dry form.

17. The vehicle for medicinal preparations according to claim 1, wherein the preparation is made in the absence of organic solvents.

18. The vehicle for medicinal preparations according to claims 1, wherein the cyclosporine-A, in a natural or synthetic form, is present as an active principle alone or mixed with further active principles.

19. The vehicle for medicinal preparations according to claim 18, wherein the active principle is finely dispersed within the particles or dissolved or adsorbed on the surface of the particles.

20. The vehicle for medicinal preparations according to claim 1, wherein the cyclosporine-A is present in an amount of between 0.01% and 70%.

21. The vehicle for medicinal preparations according to claim 1, comprising a lipid matrix, wherein the lipid matrix comprises a mixture of monoglycerides, diglycerides and triglycerides of palmitic acid and stearic acid, charged with an amount of between 0.01% and 70%, of cyclosporine-A, and is stabilized with a mixture of polyosyethylene glycerol monostearate and sodium cholate.

22. The vehicle for medicinal preparations according to claim 1 wherein a mixture of monoglycerides, diglycerides and triglycerides of palmitic acid and stearic acid comprises a lipid matrix, loaded with between 5% and 30% of cyclosporine and stabilized with lecithins, a sugar alcohol, or sugar ester, or sugar ether, sodium cholate, or their mixtures.

23. The vehicle for medicinal preparations according to claim 1, wherein a final formulation for oral and peroral administration is in the form of a dry powder in sachets for reconstitution as a suspension prior to use, as pellets, granules, tablets, effervescent tablets, capsules, and therapeutical drug release system.

24. The vehicle for medicinal preparations according to claim 1 being in the form of a final formulation for parenteral administration, as a suspension of particles, or as unit of larger dimensions for the release of the medicinal preparation.

25. The vehicle for medicinal preparations according to claim 1 being in the form of a final preparation for dermal use on skin or mucosae.

26. The vehicle for medicinal preparations according to claim 1 is a therapeutic treatment formulation containing cyclosporine-A, where the therapeutic formulation generates a mean concentration of from 300 ng/ml up to 1,000 ng/ml in the blood under stationary conditions in an absence of high initial mean concentrations in the blood of substantially higher than 1500 ng/ml.

27. A vehicle for medicinal preparations according to claim 26, which generates a mean concentration in the blood, under stationary conditions, for a period of at least 5 hours.

28. A therapeutic treatment with formulations of cyclosporine-A of claim 1, which generates a mean concentration in the blood under stationary conditions of from 300 ng/ml up to more than 1000 ng/ml, in the absence of high initial mean concentrations in the blood of substantially higher than 1500 ng/ml.

29. Therapeutic treatment according to claim 28, wherein a mean concentration in the blood, under stationary conditions, is maintained up to at least 5 hours.

30. The vehicle for medicinal preparations according to claim 25, in the form of an ointment, cream, paste, pencil, gel, or lotion.

* * * * *